US010835533B2

(12) United States Patent
Allen et al.

(10) Patent No.: US 10,835,533 B2
(45) Date of Patent: Nov. 17, 2020

(54) 1 -((3S,4R)-4-(3-FLUOROPHENYL)-1-(2-METHOXYETHYL)PYRROLIDIN-3-YL)-3-(4-METHYL-3-(2-METHYLPYRIMIDIN-5-YL)-1-PHENYL-1H-PYRAZOL-5-YL)UREA AS A TRKA KINASE INHIBITOR

(71) Applicant: Array BioPharma Inc., Boulder, CO (US)

(72) Inventors: Shelley Allen, Boulder, CO (US); Steven W. Andrews, Boulder, CO (US); Brian Baer, Boulder, CO (US); Zackary Crane, Loveland, CO (US); Weidong Liu, Superior, CO (US); Daniel John Watson, Lafayette, CO (US)

(73) Assignee: Array BioPharma Inc., Boulder, CO (US)

( * ) Notice: Subject to any disclaimer, the term of this patent is extended or adjusted under 35 U.S.C. 154(b) by 284 days.

(21) Appl. No.: 15/311,148

(22) PCT Filed: May 14, 2015

(86) PCT No.: PCT/US2015/030795

§ 371 (c)(1),
(2) Date: Nov. 14, 2016

(87) PCT Pub. No.: WO2015/175788

PCT Pub. Date: Nov. 19, 2015

(65) Prior Publication Data

US 2017/0087156 A1 Mar. 30, 2017

Related U.S. Application Data

(60) Provisional application No. 61/993,426, filed on May 15, 2014.

(51) Int. Cl.

| | |
|---|---|
| ***A61K 31/506*** | (2006.01) |
| ***C07D 403/14*** | (2006.01) |
| ***A61K 45/06*** | (2006.01) |
| ***C07D 401/14*** | (2006.01) |
| ***C07D 405/14*** | (2006.01) |
| ***C07D 403/12*** | (2006.01) |
| ***A61K 9/00*** | (2006.01) |
| ***C07D 207/16*** | (2006.01) |

(52) U.S. Cl.

CPC .......... *A61K 31/506* (2013.01); *A61K 9/0053* (2013.01); *A61K 45/06* (2013.01); *C07D 207/16* (2013.01); *C07D 401/14* (2013.01); *C07D 403/12* (2013.01); *C07D 403/14* (2013.01); *C07D 405/14* (2013.01)

(58) Field of Classification Search

CPC .................................................... A61K 31/506

See application file for complete search history.

(56) References Cited

U.S. PATENT DOCUMENTS

| | | | |
|---|---|---|---|
| 5,849,779 | A | 12/1998 | Hirota et al. |
| 5,998,424 | A | 12/1999 | Galemmo, Jr. et al. |
| 6,197,798 | B1 | 3/2001 | Fink et al. |
| 6,410,533 | B1 | 6/2002 | Hirth et al. |
| 7,223,782 | B2 | 5/2007 | Atkinson et al. |
| 7,625,915 | B2 | 12/2009 | Dumas et al. |
| 8,592,454 | B2 | 11/2013 | Shirai et al. |
| 9,163,017 | B2 | 10/2015 | Degoey et al. |
| 9,546,156 | B2 | 1/2017 | Allen et al. |
| 9,562,055 | B2 | 2/2017 | Allen et al. |

(Continued)

FOREIGN PATENT DOCUMENTS

| | | |
|---|---|---|
| EP | 0761658 A1 | 12/1997 |
| EP | 1043995 B1 | 11/2006 |

(Continued)

OTHER PUBLICATIONS

Chilean Office Action, for corresponding CL Application No. 2016-02900, English translation, 11 pages, received Dec. 14, 2017.

(Continued)

*Primary Examiner* — Yong S. Chong

(74) *Attorney, Agent, or Firm* — Viksnins Harris Padys Malen LLP

(57) ABSTRACT

Provided is Compound (I) or a pharmaceutically acceptable salt thereof, which is an inhibitor of TrkA kinase and is useful in the treatment of diseases which can be treated with a TrkA kinase inhibitor such as pain, cancer, inflammation and inflammatory diseases, neurodegenerative diseases, certain infectious diseases, Sjogren's syndrome, endometriosis, diabetic peripheral neuropathy, prostatitis, pelvic pain syndrome, diseases related to an imbalance of the regulation of bone remodeling, and diseases resulting from Connective Tissue Growth Factor aberrant signaling.

1

O N NH F O HN N N N N

5 Claims, 4 Drawing Sheets

(56) References Cited

U.S. PATENT DOCUMENTS

| | | | |
|---|---|---|---|
| 2009/0105476 | A1 | 4/2009 | Fairhurs et al. |
| 2009/0163710 | A1 | 6/2009 | Gaul |
| 2011/0178060 | A1 | 7/2011 | Shiral et al. |
| 2016/0272592 | A1 | 9/2016 | Blake et al. |
| 2016/0280682 | A1 | 9/2016 | Allen et al. |
| 2016/0280690 | A1 | 9/2016 | Brandhuber et al. |
| 2016/0280692 | A1 | 9/2016 | Andrews et al. |
| 2016/0280702 | A1 | 9/2016 | Brandhuber et al. |
| 2016/0297758 | A1 | 10/2016 | Allen et al. |
| 2016/0297796 | A1 | 10/2016 | Allen et al. |
| 2016/0355517 | A1 | 12/2016 | Allen et al. |
| 2016/0355521 | A1 | 12/2016 | Allen et al. |

FOREIGN PATENT DOCUMENTS

| | | | |
|---|---|---|---|
| EP | 2033955 | A1 | 3/2009 |
| EP | 1451160 | B1 | 1/2010 |
| EP | 2336105 | B9 | 9/2014 |
| JP | 2005206527 | A | 8/2005 |
| WO | 1998004521 | A1 | 2/1998 |
| WO | 1999023091 | A1 | 5/1999 |
| WO | 199932110 | A1 | 7/1999 |
| WO | 1999032111 | A1 | 7/1999 |
| WO | 2000039116 | A1 | 7/2000 |
| WO | 2000043384 | A1 | 7/2000 |
| WO | 2001012188 | A1 | 2/2001 |
| WO | 2001028987 | A1 | 4/2001 |
| WO | 2002002525 | A2 | 1/2002 |
| WO | 2002088101 | A2 | 11/2002 |
| WO | 2002090326 | A1 | 11/2002 |
| WO | 2003037274 | A2 | 5/2003 |
| WO | 2003045920 | A1 | 6/2003 |
| WO | 2003051275 | A2 | 6/2003 |
| WO | 2004005262 | A2 | 1/2004 |
| WO | 2004032870 | A2 | 4/2004 |
| WO | 2004039814 | A1 | 5/2004 |
| WO | 2004060305 | A2 | 7/2004 |
| WO | 2004060306 | A2 | 7/2004 |
| WO | 2004061084 | A2 | 7/2004 |
| WO | 2004111009 | A1 | 12/2004 |
| WO | 2005024755 | A2 | 3/2005 |
| WO | 2005048948 | A2 | 6/2005 |
| WO | 2005110994 | A2 | 11/2005 |
| WO | 2006014290 | A2 | 2/2006 |
| WO | 2006068591 | A1 | 6/2006 |
| WO | 2006070198 | A1 | 7/2006 |
| WO | 2006071940 | A2 | 7/2006 |
| WO | 2006081034 | A2 | 8/2006 |
| WO | 2006123257 | A2 | 11/2006 |
| WO | 2007008917 | A2 | 1/2007 |
| WO | 2007059202 | A2 | 5/2007 |
| WO | 2007061882 | A2 | 5/2007 |
| WO | 2007063009 | A1 | 6/2007 |
| WO | 2007064872 | A2 | 6/2007 |
| WO | 2008016811 | A2 | 2/2008 |
| WO | 2008018822 | A1 | 2/2008 |
| WO | 2008021859 | A1 | 2/2008 |
| WO | 2008033999 | A2 | 3/2008 |
| WO | 2008034008 | A2 | 3/2008 |
| WO | 2008046003 | A2 | 4/2008 |
| WO | 2008131276 | A1 | 10/2008 |
| WO | 2008150899 | A1 | 12/2008 |
| WO | 2009007426 | A1 | 1/2009 |
| WO | 2009140128 | A2 | 11/2009 |
| WO | 2010032856 | A1 | 3/2010 |
| WO | 2010033941 | A1 | 3/2010 |
| WO | 2010040663 | A1 | 4/2010 |
| WO | 2010048314 | A1 | 4/2010 |
| WO | 2010059719 | A2 | 5/2010 |
| WO | 2010075376 | A2 | 7/2010 |
| WO | 2010077680 | A2 | 7/2010 |
| WO | 2010104488 | A1 | 9/2010 |
| WO | 2010125799 | A1 | 11/2010 |
| WO | 2011006074 | A1 | 1/2011 |
| WO | 2011032291 | A1 | 3/2011 |
| WO | 2011146336 | A1 | 11/2011 |
| WO | 2012158413 | A2 | 11/2012 |
| WO | 2013063214 | A1 | 5/2013 |
| WO | 2013096226 | A1 | 6/2013 |
| WO | 2013176970 | A1 | 11/2013 |
| WO | 2014052563 | A1 | 4/2014 |
| WO | 2014052566 | A1 | 4/2014 |
| WO | 2014078322 | A1 | 5/2014 |
| WO | 2014078323 | A1 | 5/2014 |
| WO | 2014078325 | A1 | 5/2014 |
| WO | 2014078328 | A1 | 5/2014 |
| WO | 2014078331 | A1 | 5/2014 |
| WO | 2014078372 | A1 | 5/2014 |
| WO | 2014078408 | A1 | 5/2014 |
| WO | 2014078417 | A1 | 5/2014 |
| WO | 2014078454 | A1 | 5/2014 |
| WO | 2015039333 | A1 | 3/2015 |
| WO | 2015042085 | A2 | 3/2015 |
| WO | 2014078378 | A1 | 5/2015 |
| WO | 2015175788 | A1 | 11/2015 |

OTHER PUBLICATIONS

McMahon, et al., "The biological effects of endogenous nerve growth factor on adult sensory neurons revealed by a trkA-IgG fusion molecule", Nat Med 1, 774-780 (1995).

medicinenet.com, "Definition of Cancer", http://www.medterms.com, 1 page (2004).

Medlineplus, "Infections", https://medlineplus.gov/infections.html, 10 pages (2016).

Meyer, et al., "Remarkable leukemogenic potency and quality of a constitutively active neurotrophin receptor, deltaTrkA", Leukemia 21(10), 2171-2180 (2007).

Michelotti, et al., "Two classes of p38a MAP kinase inhibitors having a common diphenylether core but exhibiting divergent binding modes", Bioorganic & Medicinal Chemistry Letter, vol. 15, p. 5274-5279 (2005).

Miyazaki, et al., "Design and Effective synthesis of novel templates, 3, 7-diphenyl-4-amino-thieno and furo-[3,2-c] pyridines as protein kinase inhibitors and in vitro evaluation targeting angiogenetic kinases", Bioorganic & Medicinal chemistry Letters, vol. 17, p. 250-254 (2007).

Montalban, et al., "KR-003048, a potent, orally active inhibitor of p38 mitogen-activated protein kinase", European J Pharmacology 632(1-3), 93-102 (2010).

Morissette, et al., "High-throughput crystallization: polymorphs, salts, co-crystals and solvates of pharmaceutical solids", Advanced Drug Delivery Reviews, vol. 56, 275-300 (2004).

Mulvihill, et al., "Novel 2-phenylquinolin-7-yl-dervied imidazo[1,5-a]pyrazines as potent insulin-like growth factor-I receptor (IGF-IR) inhibitors", Bioorganic & Medicinal Chemistry, vol. 16, p. 1359-1375 (2008).

Nakagawara, "Trk receptor tyrosine kinases: a bridge between cancer and neural development", Cancer Letters 169, 107-114 (2001).

Patapoutian, et al., "Trk receptors: mediators of neurotrophin action", Current Opinion in Neurobiology 11, 272-280 (2001).

Patent Cooperation Treaty, International Searching Authority, Search Report and Written Opinion for PCT/US2015/030795, 11 pages, dated Jul. 31, 2015.

Pierottia, et al., "Oncogenic rearrangements of the NTRK1/NGF receptor", Cancer Letters 232, 90-98 (2006).

Pinski, et al., "Trk receptor inhibition induces apoptosis of proliferating but not quiescent human osteoblasts", Cancer Research 62, 986-989 (2002).

Ramer, et al. "Adrenergic innervation of rat sensory ganglia following proximal or distal painful sciatic neuropathy: distinct mechanisms revealed by anti-NGF treatment", Eur J Neurosci 11, 837-846 (1999).

Rautio, et al., "Prodrugs: design and clinical applications", Nature Reviews, vol. 7, p. 255-270 (2008).

Raychaudhuri, et al., "K252a, a high-affinity nerve growth factor receptor blocker, improves psoriasis: an in vivo study using the

(56) References Cited

OTHER PUBLICATIONS severe combined immunodeficient mouse-human skin model", J Investigative Dermatology 122(3), 812-819 (2004).
Ricci, et al., "Neurotrophins and neurotrophin receptors in human lung cancer", American Journal of Respiratory Cell and Molecular Biology 25(4), 439-446 (2001).
Ro, et al., "Effect of NGF and anti-NGF on neuropathic pain in rats following chronic constriction injury of the sciatic nerve", Pain 79(2-3), 265-274 (1999).
Rouhi, et al., "The Right Stuff", Chemical and Engineering News: Science and Technology, vol. 81, No. 8, 32-35 (2003).
Shelton, et al., "Nerve growth factor mediates hyperalgesia and cachexia in auto-immune arthritis", Pain 116, 8-16 (2005).
Theodosiou, et al., "Hyperalgesia due to nerve damage: role of nerve growth factor", Pain 81, 245-255 (1999).
Truzzi, et al., "Neurotrophins in healthy and diseased skin", Dermato-Endocrinology, 3(1), 32-36 (2011).
Tsuzuki, et al., "Practical Synthesis of (3S,4S)-3-methoxy-4-methylaminopyrrolidine", Tetrahedron: Asymmetry, vol. 12, 2989-2997 (2001).
UCSF Medical Center, "Neurological Disorders", https://www.ucsfhealth.org/conditions/neurological_disorders, 1 page (2016).
Vicentini, et al., "Synthesis of N-Alkyl-N-(4-Diazo-5-Pyrazolyl)Ureas and their conversion into Pyrazolo[3,4-d][1,2,3] Triazole and Pyrazolo[3,4-d]Oxazole Derivatives", Heterocycles, vol. 32, No. 4. p. 727-734 (1991).
Vogelstein, et al., "Cancer Genes and the Pathways they control", Nature Medicine, vol. 10, p. 789-799 (2004).
Wadhwa, et al., "Expression of the neurotrophin receptors Trk A and Trk B in adult human astrocytoma and glioblastoma", Journal of Biosciences 28(2), 181-188 (2003).
Wang, et al., "Trk kinase inhibitors as new treatments for cancer and pain", Expert Opinion on Therapeutic Patents, 19(3), 305-319 (2009).
Wolff, "Burger's Medicinal Chemistry and Drug Discovery", Fifth Edition, vol. 1: Principles and Practice, 975-977 (1995).
Wong, et al., "Pharmacokinetic Optimization of Class-Selective Histone Deacetylase Inhibitors and Identification of Associated Candidate Predictive Biomarkers of Hepatocellular Carcinoma Tumor Response", Journal of Medicinal Chemistry, vol. 55, 8903-8925, (2012).
Woolf, et al., "Nerve growth factor contributes to the generation of inflammatory sensory hypersensitivity", Neuroscience 62, 327-331 (1994).
Yilmaz, et al., "Theraputic targeting of Trk supresses tumor proliferation and enhances cisplatin activity in HNSCC", Cancer Biology & Therapy 10(6), 644-653 (2010).
Zahn, et al., "Effect of blockade of nerve growth factor and tumor necrosis factor on pain behaviors after plantar incision", J Pain 5, 157-163 (2004).
Adriaenssens, et al., "Nerve growth factor is a potential therapeutic target in breast cancer", Cancer Res 68(2), 346-351 (2008).
Aisen, "Alzheimer's Disease Therapeutic Research: The Path Forward", Alzheimer's Research and Therapy, vol. 1, No. 2, p. 1-6 (2009).
Asaumi, et al., "Expression of neurotrophins and their receptors (TRK) during fracture healing", Bone 26(6), 625-633 (2000).
Banker, et al., "Modem Pharmaceutics", Modem Pharmaceutics, Third Edition, Revised and Expanded, pp. 451 and 596 (1996).
Bardelli, "Mutational analysis of the tyrosine kinome in colorectal cancers", Science 300, 949 (2003).
Beaumont, et al., "Design of Ester Prodrugs to Enhance Oral Absorption of Poorly Permeable Compounds: Challenges to the Discovery Scientist", Current Drug Metabolism 4, 461-485 (2003).
Bhattacharya, et al., "Identification of novel series of pyrazole and indole-urea based DFG-out PYK2 inhibitors", Bioorganic & Medicinal Chemistry Letters 22(24), 7523-7592 (2012).
Bouhana, et al., "Comparison of Analgesic Effects of an Allosteric Inhibitor of TrkA to that of an ATP Site Inhibitor of the pan-Trk Axis in a Rodent Model of Inflammatory Pain", Gordon Conference, Salve Regina University, Newport, RI, 1 page, Jun. 7, 2011.
Brodeur, et al., "Neuroblastoma: biological insights into a clinical enigma", Nat Rev Cancer 3, 203-216 (2003).
Brodeur, et al., "Trk Receptor Expression and Inhibition in Neuroblastomas", Clin Cancer Res., vol. 15, No. 10 (2009).
Bruno, "1-Methyl and 1-(2-hydroxyalkyl)-5-(3-alkyl/cycloalkyl/phenyl/naphthylureido)-1H-pyrazole-4-carboxylic acid ethyl esters as potent human neutrophil chemotaxis inhibitors", Bioorganic & Medicinal Chemistry 17(9), 3379-3387 (2009).
Burger, et al., "5-Amino-4-trifluormethylthiazole and 5-Aminomethy1-4-trifluormethyl-1,3-azole: Nützliche Ausgangssubstanzen für Wirkstoff-Synthesen", Synthesis 4, 360-365 (1990).
Byrn, et al., "Solid-State Chemistry of Drugs", Solid-State Chemistry of Drugs, Chapter 11 Hydrates and Solvates, 233-247, Second Edition (1999).
Chambers, et al., "Synthesis and structure-activity relationships of a series of (1H-pyrazol-4-yl)acetamide antagonists of the P2X7 receptor", Bioorganic & Medicinal Chemistry Letters 20(10), 3161-3164 (2010).
Costa Rican Office Action, Opposition letter from P/Asociacion De La Industria Farmaceutica Nacional (ASIFN) dated Oct. 8, 2015, received in related Costa Rican patent application No. 2015-0264, 10 pages.
Davidson, et al., "Expression and activation of the nerve growth factor receptor TrkA in serous ovarian carcinoma", Clin Cancer Res 9, 2248-2259 (2003).
Davies, et al., "Asymmetric Synthesis of 3, 4-anti- and 3, 4-syn-substituted Aminopyrrolidines via Lithium Amide Conjugate Addition", Organic and Biomolecular Chemistry, vol. 5, 1961-1969 (2007).
De Melo-Jorge, et al., "The Chagas' disease parasite Trypanosoma cruzi exploits nerve growth factor receptor TrkA to infect mammalian hosts", Cell Host & Microbe 1(4), 251-261 (2007).
Delafoy, et al., "Role of nerve growth factor in the trinitrobenzene sulfonic acid-induced colonic hypersensitivity", Pain 105, 489-497 (2003).
Desmet, et al., "The neurotrophic receptor TrkB: a drug target in anti-cancer therapy?", Cell. Mol. Life Sci. vol. 63, p. 755-759 (2006).
Di Mola, et al., "Nerve growth factor and Trk high affinity receptor (TrkA) gene expression in inflammatory bowel disease", Gut 46(5), 670-678 (2000).
Dou, et al., "Increased nerve growth factor and its receptors in atopic dermatitis: an immunohistochemical study", Archives of Dermatological Research 298(1), 31-37 (2006).
Du, et al., "Expression of NGF family and their receptors in gastric carcinoma: A cDNA microarray study", World Journal of Gastroenterology 9(7), 1431-1434 (2003).
Eguchi, et al., "Fusion of ETV6 to neurotrophin-3 receptor TRKC in acute myeloid leukemia with t(12;15)(p13;q25)", Blood 93(4), 1355-1363 (1999).
El Haddad, et al., "A convenient synthesis of pyrazolo[3,4-d]pyrimidine-4,6-dione and pyrazolo[4,3-d]pyrimidine-5,7-dione derivatives", J Heterocyclic Chem 37(5), 1247-1252 (2000).
Eliav, et al. "The kappa opioid agonist GR89 696 blocks hyperalgesia and allodynia in rat models of peripheral neuntis and neuropathy", Pain 79 (2-3), 255-264 (1999).
Euthus, et al., "ETV6-NTRK3—Trk-ing the primary event in human secretory breast cancer", Cancer Cell 2(5), 347-348 (2002).
Felder, "The generation of purinome-targeted libraries as a means to diversify ATP-mimetic chemical classes for lead finding", Mol Divers, vol. 16, p. 27-51 (2012).
Freund-Michel, et al., "The nerve growth factor and its receptors in airway inflammatory diseases", Pharmacology & Therapeutics 117(1), 52-76 (2008).
Gingrich, et al., "Synthesis, Modeling, and In Vitro Activity of (3'S)-epi-K-252a Analogues. Elucidating the Stereochemical Requirements of the 3'-Sugar Alcohol on trkA Tyrosine Kinase Activity", J. Med. Chem. vol. 48, p. 3776-3783 (2005).
Greco, et al., "Rearrangements of NTRK1 gene in papillary thyroid carcinoma", Molecular and Cellular Endocrinology 321(1), 44-49 (2010).

(56) References Cited

OTHER PUBLICATIONS

Gruber-Olipitz, et al., "Synthesis, chaperoning, and metabolism of proteins are regulated by NT-3/TrkC signaling in the medulloblastoma cell line DAOY", Journal of Proteome Research 7(5), 1932-1944 (2008).
Gwak, et al., "Attenuation of mechanical hyperalgesia following spinal cord injury by administration of antibodies to nerve growth factor in the rat", Neurosci Left 336, 117-120 (2003).
Han, et al., "Structural characterization of proline-rich tyrosine kinase 2 (PYK2) reveals a unique (DFG-out) conformation and enables inhibitor design", J Biological Chem 284(19), 13199-13201 (2009).
Herzberg, et al., "NGF involvement in pain induced by chronic constriction injury of the rat sciatic nerve", Neuroreport 8, 1613-1618 (1997).
Hu, et al., "Decrease in bladder overactivity with REN1820 in rats with cyclophosphamide induced cystitis", Journal of Urology 173(3), 1016-1021 (2005).
Jaggar, et al., "Inflammation of the rat urinary bladder is associated with a referred thermal hyperalgesia which is nerve growth factor dependent", Br J Anaesth 83, 442-448 (1999).
Japanese Office Action, dated Nov. 13, 2015 in JP Patent Application No. 2014-510416 and English Translation; 9 pages.
Jiang, et al., "3,5-Disubstituted quinolines as novel c-Jun N-terminal kinase inhibitors", Bioorganic & Medicinal Chemistry Letters, vol. 17, p. 6378-6382 (2007).
Jin, et al., "TrkC plays an essential role in breast tumor growth and metastasis", Carcinogenesis 31(11), 1939-1947 (2010).
Kane, et al., "Ureas of 5-aminopyrazole and 2-aminothiazole inhibit growth of gram-positive bacteria", Biorg Med Chem Lett 13(24), 4463-4466 (2003).
Kaymakcioglu, et al., "Synthesis and biological evaluation of new N-substituted-N'-(3,5-di/1,3,5-trimethylpyrazole-4-yl)thiourea/urea derivatives", European Journal of Pharmaceutical Sciences 26(1), 97-103 (2005).
Lamb, et al., "Nerve growth factor and gastric hyperalgesia in the rat", Neurogastroenterol. Motil. 15, 355-361 (2003).
Li, et al., Chinese Journal of Cancer Prevention and Treatment 16(6), 428-430 [with English Abstract] (2009).
Li, et al., "Lumbar 5 ventral root transection-induced upregulation of nerve growth factor in sensory neurons and their target tissues: a mechanism in neuropathic pain", Mol Cell Neurosci 23, 232-250 (2003).
Lippard, "The Art of Chemistry", Nature, vol. 416, p. 587 (2002).
Liu, et al., "Synthesis and SAR of 1,9-dihydro-9-hydroxypyrazolo[3,4-b]quinolin-4-ones as novel, selective c-Jun N-terminal kinase inhibitors", Bioorganic & Medicinal Chemistry Letters, vol. 16, p. 2590-2594 (2006).
Ma, et al., "The progressive tactile hyperalgesia induced by peripheral inflammation is nerve growth factor dependent", NeuroReport 8, 807-810 (1997).
Mantyh, et al., "Antagonism of Nerve Growth Factor-TrkA Signaling and the Relief of Pain", Anesthesiology vol. 115 (1), 189-204 (2011).
McCarthy, et al., "Tropomyosin receptor kinase inhibitors: a patent update 2009-2013", Expert Opin Ther Patents 24(7), 731-744 (2014).
Barker, A , et al., "Studies Leading to the Identification of ZD1839 (IressaTM): An Orally Active, Selective Epidermal Growth Factor Receptor Tyrosine Kinase Inhibitor Targeted to the Treatment of Cancer", Bioorganic & Medicinal chemistry Letters 11, 1911-1914 (2001).
Brown, M , et al., "Novel CCR1 antagonists with improved metabolic stability", Bioorganic & Medicinal Chemistry Letters 14, 2175-2179 (2004).
Chen, C , et al., "Identification and characterization of pyrrolidine diastereoisomers as potent functional agonists and antagonists of the human melanocortin-4 receptor", Bioorganic & Medicinal Chemistry Letters 18, 129-136 (2008).
Rosenblum, S , et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", J Med Chem 41, 973-980 (1998).
Sanguinetti, M , et al., "hERG potassium channels and cardiac arrhythmi", Nature 440, 463-469 (2006).

1-((3S,4R)-4-(3-FLUOROPHENYL)-1-(2-METHOXYETHYL)PYRROLIDIN-3-YL)-3-(4-METHYL-3-(2-METHYLPYRIMIDIN-5-YL)-1-PHENYL-1H-PYRAZOL-5-YL)UREA AS A TRKA KINASE INHIBITOR

BACKGROUND OF THE INVENTION

The present invention relates to novel compounds, to pharmaceutical compositions comprising the compounds, to processes and intermediates for making the compounds, and to the use of the compounds in therapy. More particularly, it relates to 1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea, or a pharmaceutically acceptable salt thereof, which exhibits TrkA kinase inhibition, and which is useful in the treatment of pain, cancer, inflammation/inflammatory diseases, neurodegenerative diseases, certain infectious diseases, Sjogren's syndrome, endometriosis, diabetic peripheral neuropathy, prostatitis, pelvic pain syndrome, diseases related to an imbalance of the regulation of bone remodeling, and diseases resulting from Connective Tissue Growth Factor aberrant signaling.

The current treatment regimens for pain conditions utilize several classes of compounds. The opioids (such as morphine) have several drawbacks including emetic, constipatory and negative respiratory effects, as well as the potential for addiction. Non-steroidal anti-inflammatory analgesics (NSAIDs, such as COX-1 or COX-2 types) also have drawbacks including insufficient efficacy in treating severe pain. In addition, COX-1 inhibitors can cause ulcers of the mucosa. Accordingly, there is a continuing need for new and more effective treatments for the relief of pain, especially chronic pain.

Trk's are the high affinity receptor tyrosine kinases activated by a group of soluble growth factors called neurotrophins (NT). The Trk receptor family has three members: TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trk's are widely expressed in neuronal tissue and are implicated in the maintenance, signaling and survival of neuronal cells (Patapoutian, A. et al., *Current Opinion in Neurobiology,* 2001, 11, 272-280).

Inhibitors of the Trk/neurotrophin pathway have been demonstrated to be effective in numerous pre-clinical animal models of pain. For example, antagonistic NGF and TrkA antibodies such as RN-624 have been shown to be efficacious in inflammatory and neuropathic pain animal models (Woolf, C. J. et al. (1994) *Neuroscience* 62, 327-331; Zahn, P. K. et al. (2004) *J. Pain* 5, 157-163; McMahon, S. B. et al., (1995) *Nat. Med.* 1, 774-780; Ma, Q. P. and Woolf, C. J. (1997) *NeuroReport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motil.* 15, 355-361; Jaggar, S. I. et al. (1999) *Br. J Anaesth.* 83, 442-448) and neuropathic pain animal models (Ramer, M. S. and Bisby, M. A. (1999) *Eur. J. Neurosci.* 11, 837-846; Ro, L. S. et al. (1999) *Pain* 79, 265-274; Herzberg, U. et al., (1997) *Neuroreport* 8, 1613-1618; Theodosiou, M. et al. (1999) *Pain* 81, 245-255; Li, L. et al. (2003) *Mol. Cell. Neurosci.* 23, 232-250; Gwak, Y. S. et al. (2003) *Neurosci. Lett.* 336, 117-120).

It has also been shown that NGF secreted by tumor cells and tumor invading macrophages directly stimulates TrkA located on peripheral pain fibers. Using various tumor models in both mice and rats, it was demonstrated that neutralizing NGF with a monoclonal antibody inhibits cancer related pain to a degree similar or superior to the highest tolerated dose of morphine. Because TrkA kinase may serve as a mediator of NGF driven biological responses, inhibitors of TrkA and/or other Trk kinases may provide an effective treatment for chronic pain states and cancer related pain.

Recent literature has also shown that overexpression, activation, amplification and/or mutation of Trk kinases are associated with many cancers including neuroblastoma (Brodeur, G. M., *Nat. Rev. Cancer* 2003, 3, 203-216), ovarian (Davidson. B., et al., *Clin. Cancer Res.* 2003, 9, 2248-2259), colorectal cancer (Bardelli, A., *Science* 2003, 300, 949), melanoma (Truzzi, F., et al., *Dermato-Endocrinology* 2011, 3(1), pp. 32-36), head and neck cancer (Yilmaz, T., et al., *Cancer Biology and Therapy* 2010, 10(6), pp. 644-653), gastric carcinoma (Du, J. et al., *World Journal of Gastroenterology* 2003, 9 (7), pp. 1431-1434), lung carcinoma (Ricci A., et al., *American Journal of Respiratory Cell and Molecular Biology* 25 (4), pp. 439-446), breast cancer (Jin, W., et al., *Carcinogenesis* 2010, 31 (11), pp. 1939-1947), secratory breast cancer (Euthus, D. M., et al., *Cancer Cell* 2002, 2 (5), pp. 347-348), Glioblastoma (Wadhwa, S., et al., *Journal of Biosciences* 2003, 28 (2), pp. 181-188), medulloblastoma (Gruber-Olipitz, M., et al., *Journal of Proteome Research* 2008, 7 (5), pp. 1932-1944), salivary gland cancer (Li, Y.-G., et al., *Chinese Journal of Cancer Prevention and Treatment* 2009, 16 (6), pp. 428-430), papillary thyroid carcinoma (Greco, A., et al., *Molecular and Cellular Endocrinology* 2010, 321 (1), pp. 44-49) and adult myeloid leukemia (Eguchi, M., et al., *Blood* 1999, 93 (4), pp. 1355-1363). In preclinical models of cancer, non-selective small molecule inhibitors of TrkA, B and C were efficacious in both inhibiting tumor growth and stopping tumor metastasis (Nakagawara, A. (2001) *Cancer Letters* 169:107-114; Meyer, J., et al. (2007) *Leukemia,* 21(10):2171-2180; Pierottia, M. A. and Greco A., (2006) *Cancer Letters* 232:90-98; Eric Adriaenssens, E., et al. *Cancer Res* (2008) 68:(2) 346-351). These data support the rationale for the use of Trk inhibitors for the treatment of cancer.

In addition, inhibition of the neurotrophin/Trk pathway has been shown to be effective in treatment of pre-clinical models of inflammatory diseases with NGF antibodies or non-selective small molecule inhibitors of TrkA. For example, inhibition of the neurotrophin/Trk pathway has been implicated in preclinical models of inflammatory lung diseases including asthma (Freund-Michel, V; Frossard, N., *Pharmacology & Therapeutics* (2008) 117(1), 52-76), interstitial cystitis (Hu, Vivian Y; et. al. *The Journal of Urology* (2005), 173(3), 1016-21), bladder pain syndrome (Liu, H.-T., et al., (2010) *BJU International,* 106 (11), pp. 1681-1685), inflammatory bowel diseases including ulcerative colitis and Crohn's disease (Di Mola, F. F, et. al., *Gut* (2000) 46(5), 670-678) and inflammatory skin diseases such as atopic dermatitis (Dou, Y.-C., et. al. *Archives of Dermatological Research* (2006) 298(1), 31-37), eczema and psoriasis (Raychaudhuri, S. P., et al., *J. Investigative Dermatology* (2004) 122(3), 812-819). These data support the rationale for the use of Trk inhibitors for the treatment of inflammatory diseases.

The TrkA receptor is also thought to be critical to the disease process of the parasitic infection of *Trypanosoma cruzi* (Chagas disease) in human hosts (de Melo-Jorge, M. et al., *Cell Host & Microbe* (2007) 1(4), 251-261).

Trk inhibitors may also find use in treating diseases related to an imbalance of the regulation of bone remodeling, such as osteoporosis, rheumatoid arthritis, and bone metastases. Bone metastases are a frequent complication of cancer, occurring in up to 70 percent of patients with advanced breast or prostate cancer and in approximately 15 to 30 percent of patients with carcinoma of the lung, colon, stomach, bladder, uterus, rectum, thyroid, or kidney. Osteolytic metastases can cause severe pain, pathologic fractures, life-threatening hypercalcemia, spinal cord compression, and other nerve-compression syndromes. For these reasons, bone metastasis is a serious and costly complication of cancer. Therefore, agents that can induce apoptosis of proliferating osteoblasts would be highly advantageous. Expression of TrkA receptors has been observed in the bone-forming area in mouse models of bone fracture (K. Asaumi, et al., *Bone* (2000) 26(6) 625-633). In addition, localization of NGF was observed in almost all bone-forming cells (K. Asaumi, et al., *Bone* (2000) 26(6) 625-633). Recently, it was demonstrated that a Trk inhibitor inhibits the signaling activated by neurotrophins binding to all three of the Trk receptors in human hFOB osteoblasts (J. Pinski, et al., *Cancer Research* (2002) 62, 986-989). These data support the rationale for the use of Trk inhibitors for the treatment of bone remodeling diseases, such as bone metastases in cancer patients.

Trk inhibitors may also find use in treating diseases and disorders such as Sjogren's syndrome (Fauchais, A. L., et al., (2009) *Scandinavian Journal of Rheumatology,* 38(1), pp. 50-57), endometriosis (Barcena De Arellano, M. L., et al., (2011) *Reproductive Sciences,* 18(12), pp. 1202-1210; Barcena De Arellano, et al., (2011) *Fertility and Sterility,* 95(3), pp. 1123-1126; Cattaneo, A., (2010) *Current Opinion in Molecular Therapeutics,* 12(1), pp. 94-106), diabetic peripheral neuropathy (Kim, H. C., et al., (2009) *Diabetic Medicine,* 26 (12), pp. 1228-1234; Siniscalco, D., et al., (2011) *Current Neuropharmacology,* 9(4), pp. 523-529; Ossipov, M. H., (2011) *Current Pain and Headache Reports,* 15(3), pp. 185-192), and prostatitis and pelvic pain syndrome (Watanabe, T., et al., (2011) *BJU International,* 108(2), pp. 248-251; and Miller, L. J., et al., (2002) *Urology,* 59(4), pp. 603-608).

TrkA inhibitors may also be useful for treating diseases resulting from Connective Tissue Growth Factor (CTGF, also referred to as CCN2) aberrant signaling, for example diseases involving tissue remodeling and fibrosis. CTGF is a central mediator of tissue remodeling and fibrosis (Lipson, K. E., et al., (2012), *Fibrogenesis & Tissue Repair* 2012, 5(Suppl 1):S24) and therapies that decrease CTGF signaling have proved effective as treatments of fibrosis (Li, G., et al., *J. Gene Med.,* 2006, 8:889-900). CTGF interacts with and activates TrkA (Wahab, N. A., (2005) *J. Am. Soc. Nephrol.* 16:340-351) and inhibition of this this pathway by TrkA inhibitors may prove useful in treating various fibrotic diseases such as Raynaud's Syndrome, Idiopathic pulmonary fibrosis, scarring (hypertrophic, keloid and others), cirrhosis, endomyocardial fibrosis, atrial fibrosis, myelofibrosis, progressive massive fibrosis (lung), nephrogenic systemic fibrosis, scleroderma, systemic sclerosis, arthrofibrosis and ocular fibrosis.

Several classes of small molecule inhibitors of Trk kinases said to be useful for treating pain or cancer are known (Wang, T et al., *Expert Opin. Ther. Patents* (2009) 19(3), 305-319; McCarthy C. and Walker E., *Expert Opin. Ther. Patents* 2014, 24(7):731-744).

International application publication No. WO 2010/032856 describes compounds represented by the formula

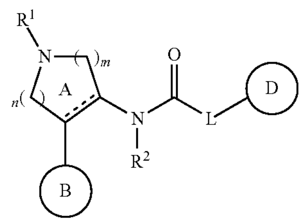

wherein ring B is an aromatic ring, ring D is an aromatic ring, and L is $NR^3$, $NR^3C(R^{4a}R^{4b})$, O or $OC(R^{4a}R^{4b})$, which are asserted to be tachykinin receptor antagonists.

International application publication No. WO 2012/158413 discloses a subset of pyrrolidinyl urea compounds as TrkA inhibitors having the general formula:

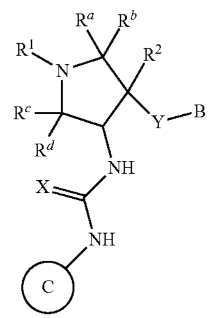

where:

Y is a bond, —O— or —$OCH_2$—;

X is O, S or NH;

$R^1$ is (1-3C alkoxy)(1-6C)alkyl, (trifluoromethoxy)(1-6C)alkyl, (1-3C sulfanyl)(1-6C)alkyl, monofluoro(1-6C)alkyl, difluoro(1-6C)alkyl, trifluoro(1-6C)alkyl, tetrafluoro(2-6C)alkyl, pentafluro(2-6C)alkyl, cyano(1-6C)alkyl, aminocarbonyl(1-6C)alkyl, hydroxy(1-6C)alkyl, dihydroxy(2-6C)alkyl, (1-6C)alkyl, (1-3Calkylamino)(1-3C)alkyl, (1-4C alkoxycarbonyl)(1-6C)alkyl, amino(1-6C)alkyl, hydroxy(1-3C alkoxy)(1-6C)alkyl, di(1-3C alkoxy)(1-6C)alkyl, (1-3C alkoxy)trifluoro(1-6C)alkyl, hydroxytrifluoro(1-6C)alkyl, (1-4C alkoxycarbonyl)(1-3C alkoxy)(1-6C)alkyl, hydroxycarbonyl(1-3C alkoxy)(1-6C)alkyl, $hetAr^5(CH_2)_{0-1}$, or $Ar^5(CH_2)_{0-1}$;

$hetAr^5$ is a 5-6 membered heteroaryl ring having 1-3 ring heteroatoms independently selected from N, O or S, wherein the ring is optionally substituted with one or more substituents independently selected from halogen, (1-6C)alkyl, (1-6C)alkoxy and $CF_3$;

$Ar^5$ is phenyl optionally substituted with one or more groups independently selected from halogen, (1-6C)alkyl, (1-6C)alkoxy, $CF_3O$—, (1-4C)alkoxycarbonyl and aminocarbonyl;

B is phenyl optionally substituted with one or more substituents independently selected from halogen, $CF_3$, $CF_3O$—, (1-4C)alkoxy, hydroxy(1-4C)alkyl, (1-6C)alkyl and CN; a 5-6 membered heteroaryl having 1-3 ring heteroatoms independently selected from N, S and O, and optionally substituted with 1-2 groups independently selected form (1-6C)alkyl, halogen, OH, $CF_3$, $NH_2$ and hydroxy(1-2C)alkyl; 1-6C alkyl; or (1-6C)alkoxy; and Ring C is formula C-1, C-2, or C-3:

C-1

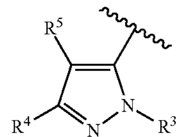

C-2

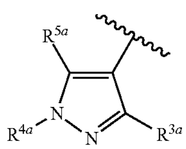

C-3

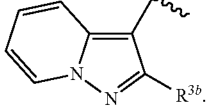

Examples of such compounds in WO 2012/158413 include the compound of Example 511 having the structure:

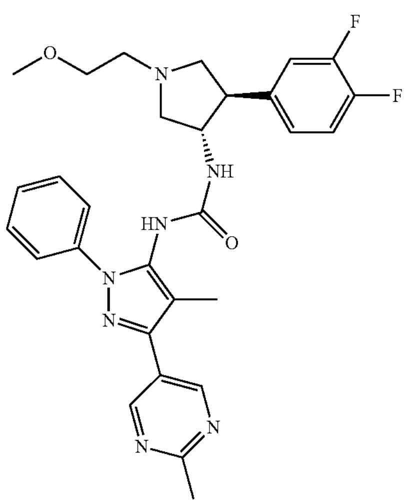 [SMILES: COCCN1C[C@@H](NC(=O)Nc2c(C)c(-c3cnc(C)nc3)nn2-c2ccccc2)[C@H](c2ccc(F)c(F)c2)C1]

which is also known as 1-((3S,4R)-4-(3,4-difluorophenyl)-1-(2-methoxyethyl)pyrrolidin-3-yl)-3-(4-methyl-3-(2-methylpyrimidin-5-yl)-1-phenyl-1H-pyrazol-5-yl)urea (hereinafter "Compound 2"), and the compound of Example 441 having the structure:

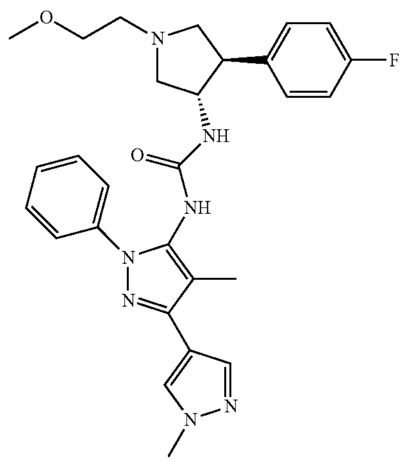 [SMILES: COCCN1C[C@@H](NC(=O)Nc2c(C)c(-c3cnn(C)c3)nn2-c2ccccc2)[C@H](c2ccc(F)cc2)C1]

which is also known has 1-(1',4-dimethyl-1-phenyl-1H,1'H-[3,4'-bipyrazol]-5-yl)-3-((3S,4R)-4-(4-fluorophenyl)-1-(2-methoxyethyl)pyrrolidin-3-yl)urea (hereinafter "Compound 3").

It has now been found that a compound having unexpected and particularly desirable properties may be obtained by selecting 2-methylpyrimidin-5-yl as the $R^4$ group and a 3-fluorophenyl as the B group.

SUMMARY OF THE INVENTION

Provided herein is Compound 1:

I

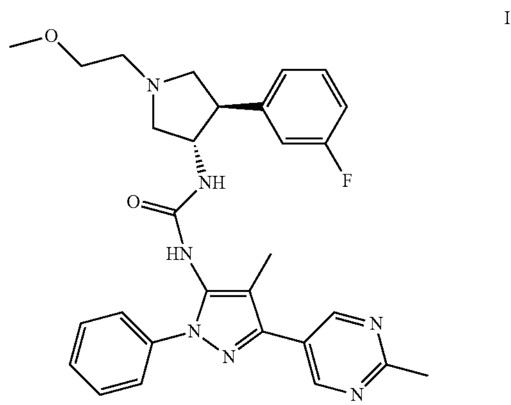

or a pharmaceutically acceptable salt thereof, which is an inhibitor of TrkA. The compound may also be described by the chemical name 1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea.

It was unexpectedly discovered that Compound 1 has a substantially lower predicted human IV (intravenous) clearance in rats relative to Compounds 2 and 3. It was also unexpectedly discovered that Compound 1 achieves a higher oral AUC (area under the plasma drug concentration-time curve) following an oral dose of 10 mg/kg in rats relative to Compounds 2 and 3. It was also unexpectedly discovered that Compound 1 achieves a higher Cmax (maximal concentration achieved in the plasma drug concentration-time curve) following an oral dose of 10 mg/kg in rats relative to Compounds 2 and 3. It was also unexpectedly discovered that Compound 1 achieves a higher trough concentration (minimal concentration achieved in the plasma drug concentration-time curve) following an oral dose of 10 mg/kg in rats relative to Compounds 2 and 3. It was also unexpectedly discovered that Compound 1 has a higher estimated inhibition of TrkA relative to Compounds 2 and 3. Compound 1 also has an unexpectedly improved peripheral-to-central nervous system distribution relative to Compound 2, as evidenced by higher plasma to brain ratio following oral administration in rats. Compound 1 also has an unexpected decrease in inhibitory activity of the hERG (the human Ether-à-go-go-Related Gene) channel relative to Compound 2.

Also provided herein are methods of treating a disease or disorder modulated by TrkA, comprising administering to a mammal in need of such treatment an effective amount of Compound 1 or a pharmaceutically acceptable salt thereof.

Also provided herein are methods of treating chronic and acute pain, including but not limited to inflammatory pain, neuropathic pain, and pain associated with cancer, surgery, or bone fracture, comprising administering to a mammal in need of such treatment an effective amount of Compound 1 or a pharmaceutically acceptable salt thereof.

Also provided herein are methods of treating cancer, comprising administering to a mammal in need of such treatment an effective amount of Compound 1 or a pharmaceutically acceptable salt thereof.

Also provided herein are methods of treating inflammation or inflammatory diseases, comprising administering to a mammal in need of such treatment an effective amount of Compound 1 or a pharmaceutically acceptable salt thereof.

Also provided herein are methods of treating neurodegenerative diseases, comprising administering to a mammal in need of such treatment an effective amount of Compound 1 or a pharmaceutically acceptable salt thereof.

Also provided herein are methods of treating prostatitis or pelvic pain syndrome, comprising administering to a mammal in need of such treatment an effective amount of Compound 1 or a pharmaceutically acceptable salt thereof.

Also provided herein are methods of treating diseases related to an imbalance of the regulation of bone remodeling, such as osteoporosis, rheumatoid arthritis, and bone metastases, comprising administering to a mammal in need of such treatment an effective amount of Compound 1 or a pharmaceutically acceptable salt thereof.

Also provided herein are methods of treating diseases and disorders selected from certain infectious diseases, Sjogren's syndrome, endometriosis, and diabetic peripheral neuropathy, comprising administering to a mammal in need of such treatment an effective amount of Compound 1 or a pharmaceutically acceptable salt thereof.

Also provided herein are methods of treating diseases resulting from Connective Tissue Growth Factor aberrant signaling, comprising administering to a mammal in need of such treatment an effective amount of Compound 1 or a pharmaceutically acceptable salt thereof.

In one embodiment, any of the above treatments comprises administering to a mammal in need of such treatment an effective amount of Compound 1 or a pharmaceutically acceptable salt thereof in combination with an additional therapeutic agent.

Also provided herein is a pharmaceutical composition comprising Compound 1 or pharmaceutically acceptable salt thereof.

Also provided herein is Compound 1 or a pharmaceutically acceptable salt thereof for use in therapy.

Also provided herein is Compound 1 or a pharmaceutically acceptable salt thereof for use in the treatment of chronic and acute pain, including but not limited to inflammatory pain, neuropathic pain, and pain associated with cancer, surgery or bone fracture.

Also provided herein is Compound 1 or a pharmaceutically acceptable salt thereof for use in the treatment of cancer.

Also provided herein is Compound 1 or a pharmaceutically acceptable salt thereof for use in the treatment of inflammation or inflammatory diseases.

Also provided herein is Compound 1 or a pharmaceutically acceptable salt thereof for use in the treatment of neurodegenerative diseases.

Also provided herein is Compound 1 or a pharmaceutically acceptable salt thereof for use in the treatment of prostatitis or pelvic pain syndrome.

Also provided herein is Compound 1 or a pharmaceutically acceptable salt thereof for use in the treatment of diseases related to an imbalance of the regulation of bone remodeling, such as osteoporosis, rheumatoid arthritis and bone metastases.

Also provided herein is Compound 1 or a pharmaceutically acceptable salt thereof for use in the treatment of certain infectious diseases, Sjogren's syndrome, endometriosis, and diabetic peripheral neuropathy.

Also provided herein is Compound 1 or a pharmaceutically acceptable salt thereof for use in the treatment of diseases resulting from Connective Tissue Growth Factor aberrant signaling.

Also provided herein is the use of Compound 1 or a pharmaceutically acceptable salt thereof in the manufacture of a medicament for the treatment of disease and disorders such as chronic and acute pain including, but not limited to, inflammatory pain, neuropathic pain, and pain associated with cancer, surgery or bone fracture.

Also provided herein is the use of Compound 1 or a pharmaceutically acceptable salt thereof in the manufacture of a medicament for the treatment of disease and disorders selected from cancer, inflammation or inflammatory diseases, neurodegenerative diseases, certain infectious diseases, Sjogren's syndrome, endometriosis, diabetic peripheral neuropathy, prostatitis, pelvic pain syndrome, and diseases related to an imbalance of the regulation of bone remodeling, such as osteoporosis, rheumatoid arthritis and bone metastases.

Also provided herein is the use of Compound 1 or a pharmaceutically acceptable salt thereof in the manufacture of a medicament for the treatment of diseases resulting from Connective Tissue Growth Factor aberrant signaling.

Also provided herein are intermediates useful for preparing TrkA inhibitory compounds such as Compound 1, and methods of preparing such intermediates.

Also provided herein are methods of preparing, methods of separation, and methods of purification of Compound 1 or a pharmaceutically acceptable salt thereof.

DETAILED DESCRIPTION OF THE INVENTION

Provided herein is Compound 1

I

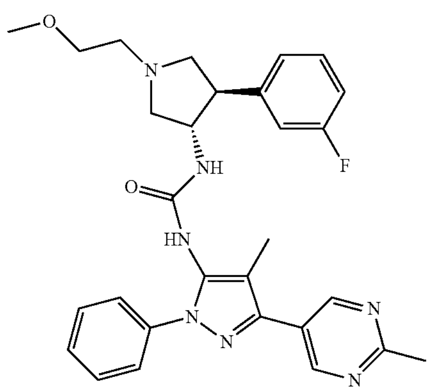

Figure 1:
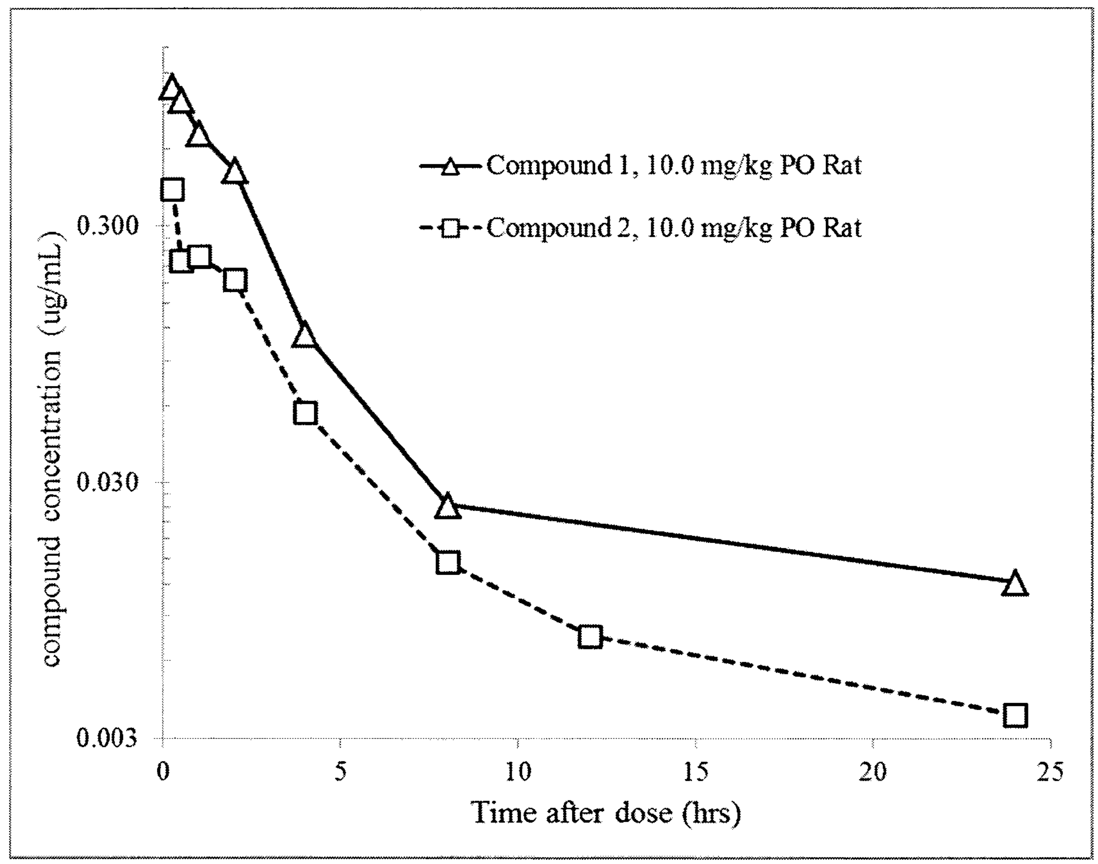
FIG. 1 is a graph comparing the plasma drug concentration (μg/mL) versus time (hours) for Compound 1 (triangles) and Compound 2 (squares) following a 10 mg/kg oral dose in rat.

or a pharmaceutically acceptable salt thereof, which is an inhibitor of TrkA. The compound may also be described by the chemical name 1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea.

It has been found that Compound 1 has particular unexpected and desirable properties. One particularly advantageous property of Compound 1 is its predicted human IV clearance, which is substantially lower relative to the predicted human IV clearance for both Compound 2 and Compound 3, as shown in Table 1.

TABLE 1

| Compound | Species | IV clearance (mL/min/kg) | microsomal clearance (mL/min/kg) | in vivo/ in vitro correction factor |
|---|---|---|---|---|
| Compound 1 | Mouse | NA * | 50 | NA * |
| | Rat | 15 | 22 | 1.47 |
| | Dog | 7.6 | 24 | 3.16 |
| | Monkey | 20 | 33 | 1.65 |
| | Human | 5 (predicted)** | 9.8 | 2.09 *** |
| Compound 2 | Mouse | 42 | 57 | 1.36 |
| | Rat | 29 | 22 | 0.76 |
| | Dog | 25 | 26 | 1.04 |
| | Monkey | 18 | 38 | 2.11 |
| | Human | 12 (predicted)** | 14 | 1.32 *** |
| Compound 3 | Mouse | 71 | 60 | 0.85 |
| | Rat | 26 | 23 | 0.88 |
| | Dog | 18 | 23 | 1.28 |
| | Monkey | 38 | 32 | 0.84 |
| | Human | 10 (predicted)** | 10 | 0.96 *** |

* Not available

**The mean correction fraction observed for pre-clinical species was used to predict the IV clearance for human.

*** Pre-clinical mean correction factor for all species tested

In Table 1, the predicted human IV clearance values were calculated from compound concentration-versus-time data in plasma collected from pre-clinical species (mouse, rat, dog and monkey) following 1 mg/kg intravenous (IV) doses. Concentrations of compound in plasma were measured by LC-MS (liquid chromatography-mass spectrometry). $AUC_{inf}$ values (Area under the plasma concentration-time curve for a dosing interval from time 0 extrapolated to infinity) for individual $C_{p/t}$ curves (concentration of the drug in plasma at any time t) were determined using linear-trapezoidal integration and first order extrapolation from terminal points of the $C_{p/t}$ curves, and clearance (CL) was calculated using Dose/$AUC_{inf}$.

The predicted hepatic clearance ($CL_h$) value was calculated by scaling the in vitro half-life ($t_{1/2}$) for stability of the compound in liver microsomes (1 mg/mL; 20 minutes) using the physical and physiological scaling factors used to predict intrinsic clearance ($CL_{int}$) and hepatic clearance ($CL_{hep}$) listed in Table 2 and employed in the following equations:

$$CL_{int} = \frac{\ln 2}{t_{1/2}}\left(\frac{D \cdot W}{C}\right)$$

$$CL_h = \frac{CL_{int} \cdot Q}{CL_{int} + Q}$$

where D is the amount of cytochrome P450-related protein per mass of liver, W is the average mass of liver present per weight of animal, C is the liver microsomal concentration, and Q is the species-dependent hepatic blood flow.

TABLE 2

| Species | W[a] | Q[b] | D[c] |
|---|---|---|---|
| Mouse | 87.0 | 90 | 50 |
| Rat | 45.0 | 70 | 45 |
| Rabbit | 30.8 | 71 | 78 |
| Dog | 32.0 | 35 | 55 |
| Monkey | 32.0 | 44 | 60 |
| Human | 25.7 | 20 | 53 |

[a]W = average mass of liver (g) per mass of animal (kg).

[b]Q = average hepatic blood flow (mL/min/kg).

[c]D (mic.) = amount of cytochrome P450-related protein (mg) per mass of liver (g).

The in vivo/in vitro correction factor was then determined by dividing the microsomal $CL_h$ value by the IV CL value. The arithmetic mean of the pre-clinical correction factors for each compound was used to predict the human IV clearance from the measured human microsomal $CL_h$ ($CL_h$/correction factor).

Figure 2:
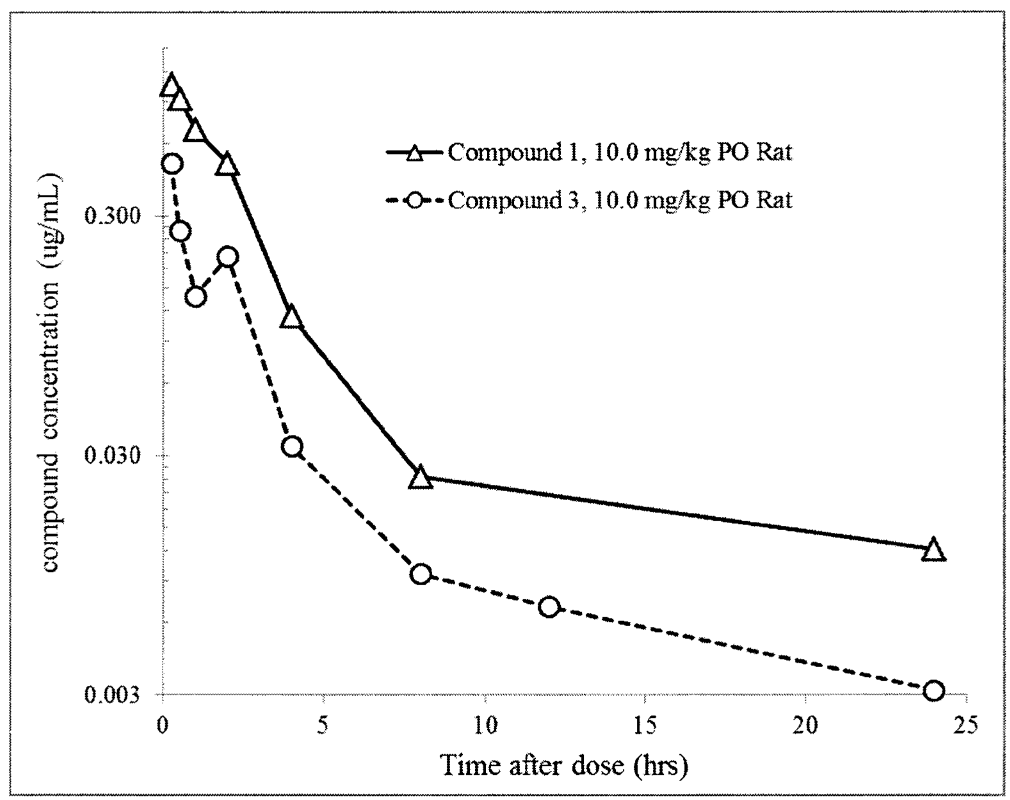
FIG. 2 is a graph comparing the plasma drug concentration (μg/mL) versus time (hours) for Compound 1 (triangles) and Compound 3 (circles) following a 10 mg/kg oral dose in rat.

Additionally, Compound 1 unexpectedly achieves a higher oral AUC (area under the plasma drug concentration-time curve), a higher Cmax (maximal concentration achieved in the plasma drug concentration-time curve), and a higher trough concentration (minimal concentration achieved in the plasma drug concentration-time curve) following an oral dose (10 mg/kg) as exemplified by its rat pharmacokinetic curves relative to Compounds 2 and 3, as shown in FIGS. 1 and 2 and summarized in Table 3.

TABLE 3

| Rat PK parameter | Compound 1 | Compound 2 | Compound 3 |
|---|---|---|---|
| AUC (μg-hr/mL) | 2.57 | 0.925 | 1.06 |
| Cmax (μg/mL) | 1.06 | 0.420 | 0.498 |
| Trough concentration (μg/mL) | 0.00134 | 0.000446 | 0.00044 |

Figure 3:
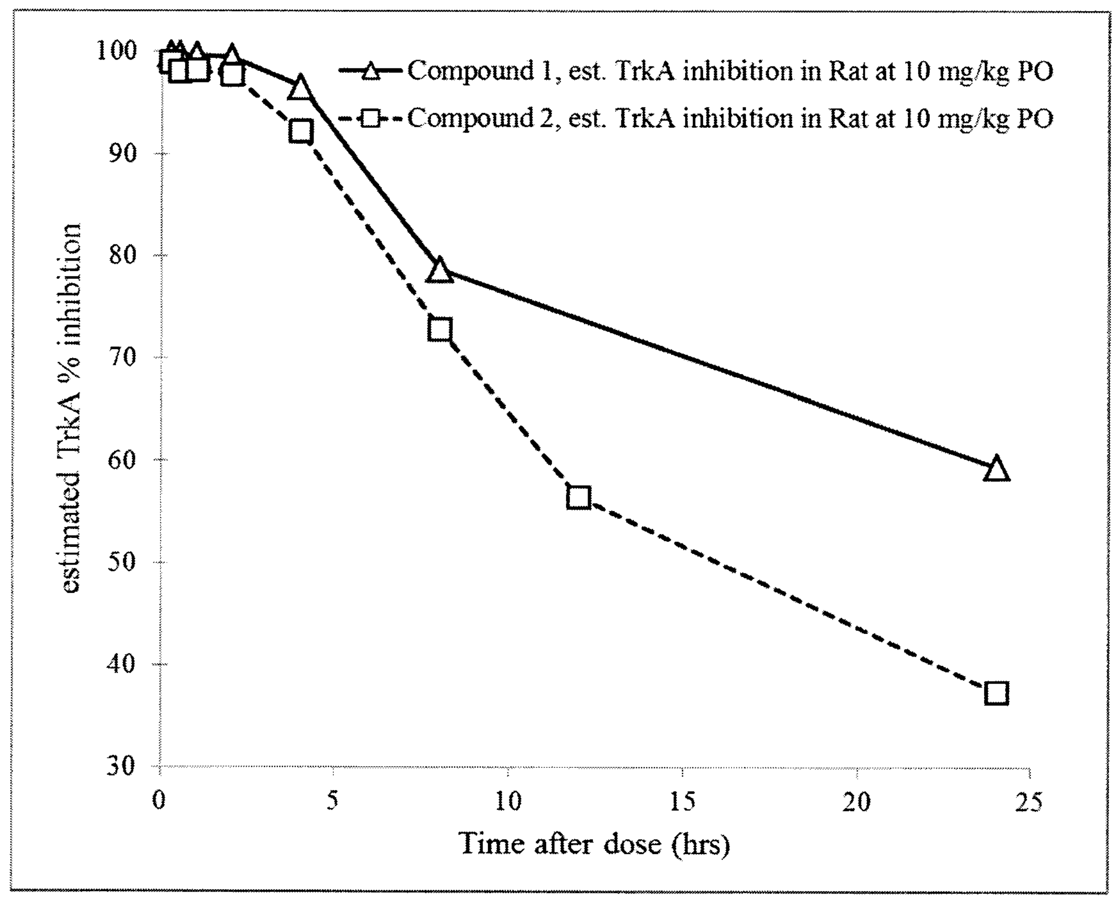
FIG. 3 is a comparison of the estimated percent TrkA inhibition versus time (hours) for Compound 1 (triangles) and Compound 2 (squares) following a 10 mg/kg oral dose in rat.
Figure 4:
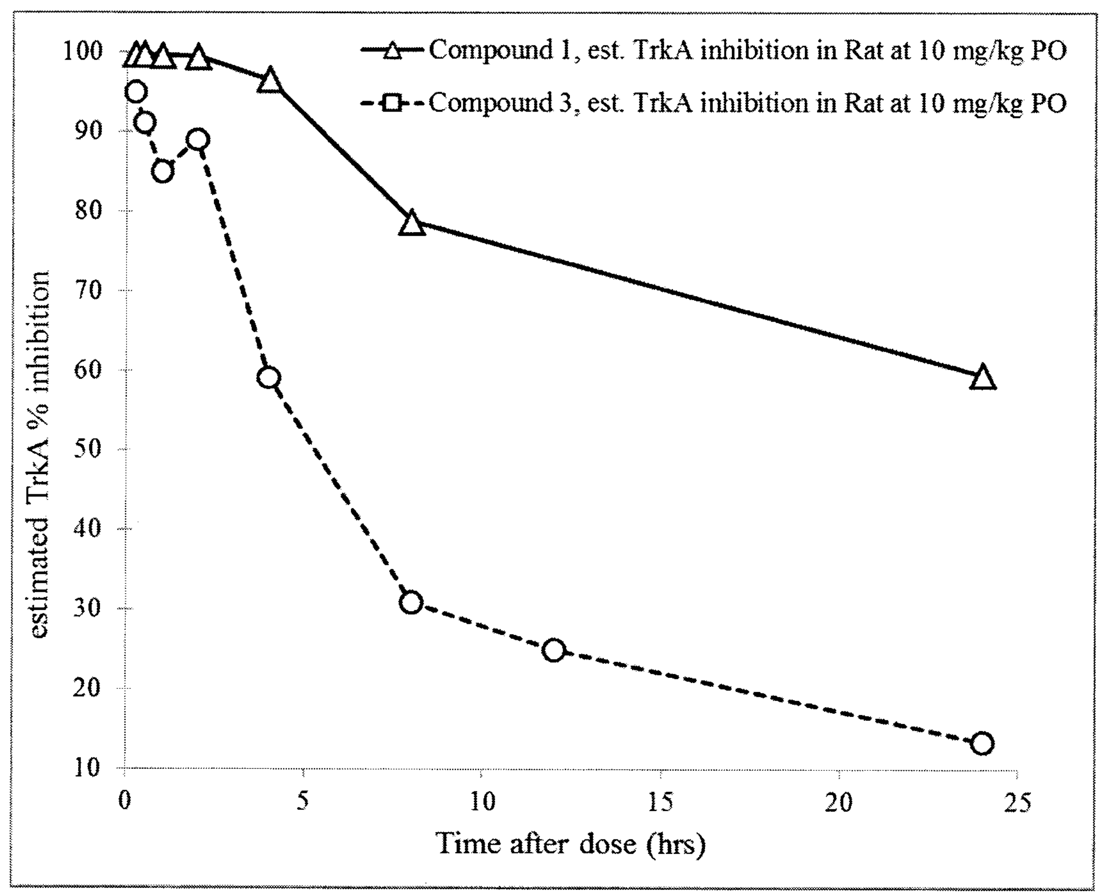
FIG. 4 is a comparison of the estimated percent TrkA inhibition versus time (hours) for Compound 1 (triangles) and Compound 3 (circles) following a 10 mg/kg oral dose in rat.

FIGS. 3 and 4 illustrate the estimated inhibition of TrkA for Compound 1 after an oral dose of 10 mg/kg in rats of relative to Compound 2, and for Compound 1 relative to Compound 3, respectively. The curves in FIGS. 3 and 4 were calculated using the following equation:

$$\text{Inhibition}(\%) = I_{min} + \frac{I_{max} - I_{min}}{1 + 10^{(\log(IC_{50}) - \log(C)) \cdot n}}$$

where $I_{min}$ and $I_{max}$ are the minimum and maximum possible inhibition of the target, respectively, $IC_{50}$ is the concentration at which the target is inhibited by 50%, C is the concentration of the inhibitor, and n is the Hill slope. As shown in FIGS. 3 and 4, the estimated inhibition of TrkA is higher for Compound 1 than for Compound 2 and Compound 3.

The lower clearance, higher AUC, higher Cmax and higher trough concentration of Compound 1 result in a greater inhibition of the TrkA receptor throughout the day following administration of Compound 1 to a patient compared to Compounds 2 and 3. This translates into a greater therapeutic efficacy for Compound 1 relative to Compounds 2 and 3. The ability to achieve improved therapeutic efficacy is important in treating patients suffering, for example, from moderate to severe pain, certain inflammatory conditions or cancer (including cancers driven by aberrant TrkA signaling).

In addition, the lower clearance of Compound 1 results in a longer half-life of the compound after administration relative to Compounds 2 and 3, resulting in a more sustained inhibition of the TrkA receptor following oral, intravenous or sub-cutaneous administration of the compound. An increased half-life has benefits in terms of providing more sustained efficacy and/or a decreased dosing frequency of the drug. Additionally, the lower human clearance and higher oral AUC of Compound 1 are advantageous in that a lower dose of Compound 1 is required to effectively inhibit the TrkA receptor and provide a given therapeutic efficacy relative to Compounds 2 and 3. Lowering the dose of a compound required for efficacy translates into improvements in the tolerability of the drug, the cost of treatment, and patient compliance with dosing regimens.

Compound 1 also has an unexpectedly improved peripheral-to-central nervous system distribution relative to Compound 2, as evidenced by higher plasma to brain ratio after oral administration in rats, as shown in Table 4. Maintaining a low brain exposure has the benefit of decreasing the risk of central nervous system related side effects, such as side effects related to cognition or motor impairment. Decreased central nervous system exposure is beneficial in that fewer or decreased side effects occur in a patient for a given therapeutic effect and/or a greater therapeutic effect is achieved before any dose-limiting side effects are observed.

Compound 1 also has an unexpectedly decreased inhibitory activity against the hERG (human Ether-à-go-go-Related Gene) channel relative to Compound 2 as shown in Table 4 Inhibition of the hERG channel function can result in a serious drug-induced (acquired) long QT syndrome side-effect, which can create a concomitant risk of sudden death. Because of the serious nature of this side effect, having the decreased inhibitory activity against hERG is highly desirable.

TABLE 4

| | Compound 1 | Compound 2 |
|---|---|---|
| Plasma:Brain ratio (Rat PO 10 mg/kg) | 21 | 11 |
| hERG $IC_{50}$ (μM) | 20 | 6.9 |

The above described unexpected properties of Compound 1 relative to Compound 2 could not reasonably be anticipated from the minor structural difference between these compounds. The only structure difference between Compound 1 versus Compound 2 is the removal of a single fluorine atom. However, it has been demonstrated in the art that the removal of a single fluorine atom from a compound does not generally provide a compound having the improved change in predicted human clearance that was observed for Compound 1 relative to Compound 2. In fact, there are a number of examples in the art with other drug motifs demonstrating that analogs having more fluorine atoms tend to have a lower in vivo clearance relative to their analogs having fewer fluorine atoms (see, for example, Barker, A. J., et al., *Bioorg. Med. Chem. Lett.* 11 (2001) 1911-1914; Rosenblum, S. B. et al., *J. Med. Chem.,* 41, (1998) 973-980; Brown, M. F. et al., *Bioorg. Med. Chem. Lett.* 14 (2004) 2175-2179). In contrast, the mono-fluoro Compound 1 has a predicted lower human clearance relative to the di-fluoro Compound 2. Similarly, the pharmacokinetic (PK) advantages of a higher Cmax, higher AUC, higher trough exposure and higher TrkA target knockdown for Compound 1 relative to Compound 2 as demonstrated by the pre-clinical rat PK data are quite remarkable and unexpected for such a small structural change.

Additionally, a comparison of the PK parameters for Compound 1 and Compound 3 demonstrates that the improved pharmacokinetics of Compound 1 is not a general phenomenon for all mono-fluoro analogs. In fact, Compound 3 demonstrated a worse projected human clearance and inferior PK values in terms of Cmax, AUC, trough exposure and TrkA target knockdown compared to Compound 1, despite having a monofluoro-substituted phenyl group. The unique combination of the methylpyrimidinyl and monofluoro-substituted phenyl moieties in Compound 1 unexpectedly provide the superior properties outlined above.

Also provided herein are pharmaceutically acceptable salts of Compound 1. Particular salts are hydrochloride salts. In one embodiment, provided herein is a monohydrochloride salt of Compound 1. In one embodiment, provided herein is a dihydrochloride salt of Compound 1.

In one embodiment, provided herein is the free base form of Compound 1.

In one embodiment, Compound 1 or its salts may be isolated in the form of solvates, and accordingly that any such solvate is included within the scope of the present invention. For example, Compound 1 or its salts can exist in unsolvated as well as solvated forms with pharmaceutically acceptable solvents such as water, ethanol, and the like.

The term "pharmaceutically acceptable" indicates that the substance or composition is compatible chemically and/or toxicologically, with the other ingredients comprising a formulation, and/or the mammal being treated therewith.

Also provided herein is a process for preparing Compound 1 or a pharmaceutically acceptable salt thereof, which comprises:

(a) reacting a compound having the formula II-A

II-A

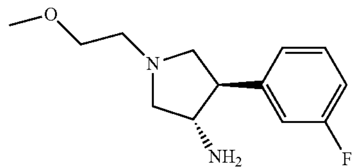

with a compound having the formula III

III

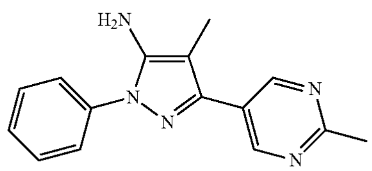

in the presence carbonyldiimidazole or triphosgene and a base; or (b) reacting a compound having the formula II-A

II-A

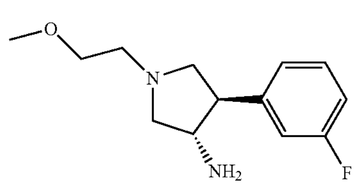

with a compound having the formula IV

IV

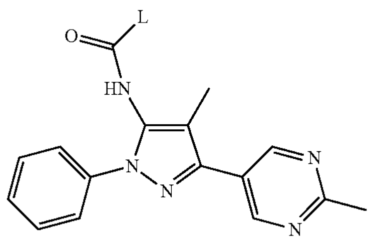

where $L^1$ is a leaving group, in the presence of a base; or (c) reacting a compound having the formula V

V

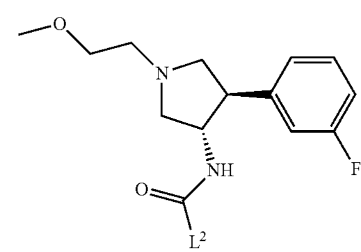

where $L^2$ is a leaving group, with a compound having the formula III

III

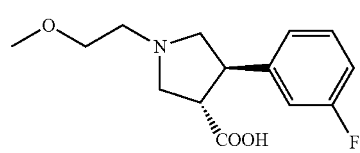

in the presence of a base; or (d) reacting a compound having the formula VI

VI

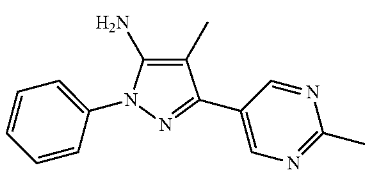

with diphenylphosphoryl azide to form an intermediate, followed by reacting the intermediate with a compound having the formula III

III

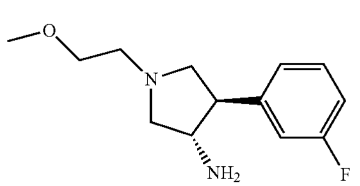

in the presence a base; or (e) reacting a compound having the formula II-A

II-A

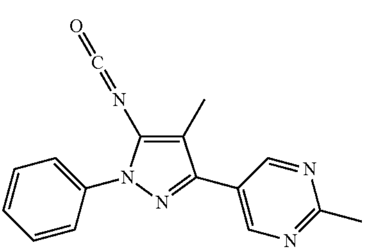

with a compound having the formula VII

VII in the presence of a base; and removing and protecting groups if present and optionally preparing a pharmaceutically acceptable salt thereof.

Referring to method (a), the base may be an amine base, such as triethylamine or diisopropylamine. Suitable solvents include dichloromethane, dichloroethane, THF, DMA and DMF. The reaction is conveniently performed at ambient temperature.

Referring to method (b), the leaving group may be, for example, phenoxy or 4-nitrophenoxy. The base may be an amine base, such as triethylamine or diisopropylamine. Suitable solvents include DMA, DMF and DCE. The reaction is conveniently performed at ambient temperature.

Referring to method (c), the leaving group may be, for example, phenoxy or 4-nitrophenoxy. The base may be an amine base, such as triethylamine or diisopropylamine. Suitable solvents include DCE, DMA and DMF. The reaction is conveniently performed at ambient temperature.

Referring to method (d), the base may be an amine base, such as triethylamine or diisopropylamine. Suitable solvents include toluene and DMF. The reaction is conveniently performed at elevated temperatures, for example the reflux temperature of the solvent.

Referring to method (e), the base may be an amine base, such as triethylamine or diisopropylamine. Suitable solvents include DCM, DCE, DMF and THF. The reaction is conveniently performed at temperatures between about 0° C. and ambient temperature.

Also provided herein is a process for preparing a racemic mixture of a compound of Formula II

II

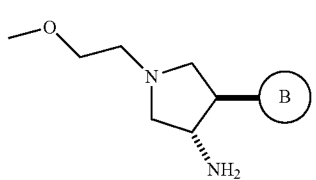

wherein the B ring and the $NH_2$ moiety are in the trans configuration. Compounds of Formula II (such as compounds of Formula II-A) are useful for preparing compounds such as TrkA inhibitory compounds, such as Compound 1.

Accordingly, provided herein is a process for preparing a racemic mixture of a compound of Formula II

II

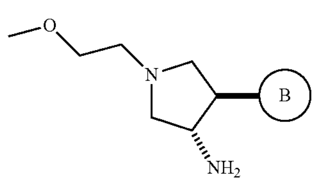

wherein:

Ring B is $Ar^1$ or $hetAr^1$;

$Ar^1$ is phenyl optionally substituted with one or more substituents independently selected from halogen, $CF_3$, $CF_3O$—, (1-4C)alkoxy, hydroxy(1-4C)alkyl, (1-6C)alkyl and CN; and $hetAr^1$ is a 5-6 membered heteroaryl having 1-3 ring heteroatoms independently selected from N, S and O, and optionally substituted with 1-2 groups independently selected form (1-6C)alkyl, halogen, OH, $CF_3$, $NH_2$ and hydroxy(1-2C)alkyl, said process comprising:

(a) reacting a compound of formula (a)

(a)

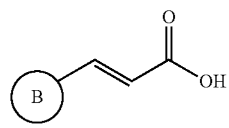

where Ring B is as defined for Formula II, with 2-methoxy-N-(methoxymethyl)-N-((trimethylsilyl)methyl)ethanamine having the formula

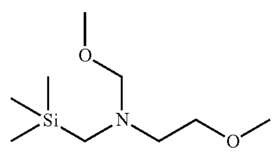

in the presence of a catalytic amount of acid, to provide a compound of formula (b)

(b)

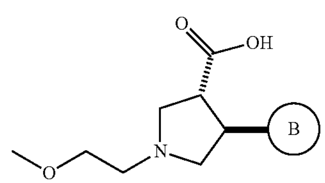

where Ring B is as defined for Formula II;

(b) reacting said compound of formula (b) with carbonyl diimidazole in the presence of a catalytic amount of imidazole hydrochloride, followed by treatment with ammonia, to provide a compound having formula (c)

(c)

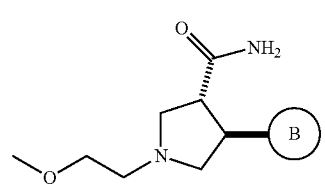

where Ring B is as defined for Formula II; and (c) reacting said compound of formula (c) with sodium hypochlorite, followed by treatment with KOH, followed by treatment with HCl, to provide said compound of Formula II as a racemic mixture of trans Formula II.

Referring to step (a), the acid may be an organic acid such as trifluoroacetic acid.

In one embodiment of the above process for preparing a racemic mixture of a compound of Formula II, Ring B is phenyl optionally substituted with one or more substituents independently selected from halogen, $CF_3$, $CF_3O$—, (1-4C)alkoxy, hydroxy(1-4C)alkyl, (1-6C)alkyl and CN.

In one embodiment of the above process for preparing a racemic mixture of a compound of Formula II, Ring B is phenyl optionally substituted with one or more substituents independently selected from halogen.

In one embodiment of the above process for preparing a racemic mixture of a compound of Formula II, Ring B is phenyl optionally substituted with one or more fluoros.

In one embodiment of the above process for preparing a racemic mixture of a compound of Formula II, Ring B is 3-fluorophenyl.

In one embodiment of the above process for preparing a racemic mixture of a compound of Formula II, Ring B is 3,4-difluorophenyl.

In one embodiment of the above process for preparing a racemic mixture of a compound of Formula II, Ring B is a 5-6 membered heteroaryl having 1-3 ring heteroatoms independently selected from N, S and O, and optionally substituted with 1-2 groups independently selected form (1-6C) alkyl, halogen, OH, $CF_3$, $NH_2$ and hydroxy(1-2C)alkyl.

In one embodiment of the above process, Ring B is a pyridyl, thiophenyl, thiazolyl, oxazolyl or isoxazolyl ring optionally substituted with 1-2 groups independently selected from (1-6C)alkyl, halogen, OH, $CF_3$, $NH_2$ and hydroxy(1-2C)alkyl.

In one embodiment of the above process for preparing a racemic mixture of a compound of Formula II, Ring B is a pyridyl, thiophenyl, thiazolyl, oxazolyl, or isoxazolyl ring optionally substituted with 1-2 groups independently selected from halogen and (1-6C)alkyl.

In one embodiment of the above process for preparing a racemic mixture of a compound of Formula II, 2-methoxy-N-(methoxymethyl)-N-((trimethylsilyl)methyl)ethanamine having the formula

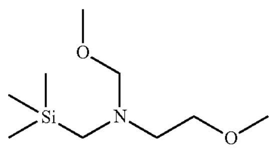

may be prepared by the process comprising:

(i) reacting (chloromethyl)trimethylsilane with 2-methoxyethanamine to provide (2-methoxy-N-((trimethylsilyl)methyl)ethanamine having the structure

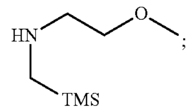

and (ii) treating said (2-methoxy-N-((trimethylsilyl)methyl) ethanamine with formaldehyde in methanol to provide said 2-methoxy-N-(methoxymethyl)-N-((trimethylsilyl)methyl) ethanamine.

Further provided herein is a process for isolating enantiomer 1 of trans Formula II, either as the free base or as the di-p-toluoyl-D-tartaric acid salt, comprising:

treating racemic trans Formula II with di-p-toluoyl-D-tartaric acid to provide the di-p-toluoyl-D-tartaric acid salt of racemic trans II;

recrystallizing the di-p-toluoyl-D-tartaric acid salt of trans II to provide the di-p-toluoyl-D-tartaric acid salt of enantiomer 1 of trans II; and optionally treating the di-p-toluoyl-D-tartaric acid salt of enantiomer 1 of trans II with an inorganic base to provide free base of enantiomer 1 of trans Formula II having the absolute configuration as illustrated:

II

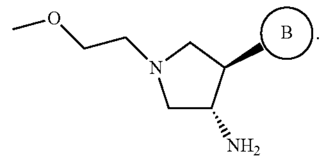

In one embodiment, the di-p-toluoyl-D-tartaric acid salt of enantiomer 1 of trans II is used to prepare compounds such as TrkA inhibitor compounds, such as Compound 1. For example, in one embodiment, the di-p-toluoyl-D-tartaric acid salt of enantiomer 1 of trans Formula II is used to prepare compounds such as TrkA inhibitor compounds, such as Compound 1 under Shotten-Baumann conditions, in which the free base of the di-p-toluoyl-D-tartaric acid salt of enantiomer 1 of trans Formula II is generated under a two-phase solvent system, consisting of water and an organic solvent (such as dichloromethane), in the presence of a base such as sodium hydroxide, and reacted with a compound having the formula IV.

In one embodiment, the free base of enantiomer 1 of trans Formula II is used to prepare compounds such as TrkA inhibitor compounds, such as Compound 1.

In one embodiment of the above process for isolating enantiomer 1 of trans Formula II, Ring B is phenyl optionally substituted with one or more substituents independently selected from halogen, $CF_3$, $CF_3O$—, (1-4C)alkoxy, hydroxy(1-4C)alkyl, (1-6C)alkyl and CN.

In one embodiment of the above process for isolating enantiomer 1 of trans Formula II, Ring B is phenyl optionally substituted with one or more substituents independently selected from halogen.

In one embodiment of the above process for isolating enantiomer 1 of trans Formula II, Ring B is phenyl optionally substituted with one or more fluoros.

In one embodiment of the above process for isolating enantiomer 1 of trans Formula II, Ring B is 3-fluorophenyl.

In one embodiment of the above process for isolating enantiomer 1 of trans Formula II, Ring B is 3,4-difluorophenyl.

In one embodiment, the above process for isolating enantiomer 1 of trans Formula II provides a method for preparing (3S,4R)-4-(3,4-difluorophenyl)-1-(2-methoxyethyl)pyrrolidin-3-amine.

In one embodiment of the above process for isolating enantiomer 1 of trans Formula II, Ring B is a 5-6 membered heteroaryl having 1-3 ring heteroatoms independently selected from N, S and O, and optionally substituted with 1-2 groups independently selected form (1-6C)alkyl, halogen, OH, $CF_3$, $NH_2$ and hydroxy(1-2C)alkyl.

In one embodiment of the above process for isolating enantiomer 1 of trans Formula II, Ring B is a pyridyl, thiophenyl, thiazolyl, oxazolyl or isoxazolyl ring optionally substituted with 1-2 groups independently selected from (1-6C)alkyl, halogen, OH, $CF_3$, $NH_2$ and hydroxy(1-2C) alkyl.

In one embodiment of the above process for isolating enantiomer 1 of trans Formula II, Ring B is a pyridyl, thiophenyl, thiazolyl, oxazolyl, or isoxazolyl ring optionally substituted with 1-2 groups independently selected from halogen and (1-6C)alkyl.

The above process for preparing a racemic mixture of a compound of Formula II offers several advantages compared to the process described in International application publication No. WO 2012/158413. For example, the process described in WO 2012/158413 includes a Nitro-Aldol reaction between a benzaldehyde reagent and nitromethane. The resulting 2-nitrovinylbenzene intermediate is then reduced by hydrogenation under high pressure. Both of these reaction steps are not amenable to synthesis on a large scale, since Nitro-Aldol reactions and the nitro intermediates derived therefrom are unstable and can be dangerous. In contrast, the above process for preparing a racemic mixture of a compound of Formula II does not use any highly hazardous chemistry and avoids nitro-containing intermediates and hydrogenations. In addition, all conditions used in the above process for preparing a racemic mixture of a compound of Formula II are within standard operating parameters typically found in pilot plants for large scale syntheses, e.g., the process does not use extreme temperatures and does not require high pressure vessels.

The ability of Compound 1 or a pharmaceutically acceptable salt thereof to act as a TrkA inhibitor may be demonstrated by the assays described in Examples A and B.

Compound 1 or a pharmaceutically acceptable salt thereof, is useful in the treatment of diseases and disorders including, but not limited to, pain, cancer, inflammation/inflammatory diseases, neurodegenerative diseases, certain infectious diseases, Sjogren's syndrome, endometriosis, diabetic peripheral neuropathy, prostatitis, pelvic pain syndrome, diseases related to an imbalance of the regulation of bone remodeling, and diseases resulting from Connective Tissue Growth Factor aberrant signaling.

As used herein, terms "treat" or "treatment" refer to therapeutic or palliative measures. Beneficial or desired clinical results include, but are not limited to, alleviation, in whole or in part, of symptoms associated with a disorder or condition, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

In certain embodiments, Compound 1 or a pharmaceutically acceptable salt thereof, is useful for preventing diseases and disorders as defined herein. The term "preventing" as used herein means the prevention of the onset, recurrence or spread, in whole or in part, of the disease or condition as described herein, or a symptom thereof, and includes to the administration of Compound 1 or a pharmaceutically acceptable salt thereof prior to the onset of symptoms.

Compound 1 or a pharmaceutically acceptable salt thereof can be used in combination with one or more additional therapeutic agents that work by the same or a different mechanism of action.

The term "pharmaceutical combination" as used herein refers to a pharmaceutical therapy resulting from the mixing or combining of more than one active ingredient and includes both fixed and non-fixed combinations of the active ingredients. The term "fixed combination" means that Compound 1 or a pharmaceutically acceptable salt thereof, and at least one additional therapeutic agent are both administered to a patient simultaneously in the form of a single entity or dosage. The term "non-fixed combination" means that Compound 1 or a pharmaceutically acceptable salt thereof, and at least one additional therapeutic agent, are administered to a patient as separate entities either simultaneously or sequentially with variable intervening time limits, wherein such administration provides effective levels of the two or more compounds in the body of the patient. These also apply to cocktail therapies, e.g. the administration of three or more active ingredients.

As used herein, the term "co-administering" is meant to encompass administration of the selected therapeutic agents to a single patient, and is intended to include treatment regimens in which the agents are administered by the same or different route of administration or at the same or different times. This term encompasses administration of two or more agents to a mammal so that both agents and/or their metabolites are present in the mammal at the same time. It includes simultaneous administration in separate compositions, administration at different times in separate compositions, and/or administration in a composition in which both agents are present. In one embodiment, the compound(s) of the invention and the other therapeutic agent(s) are administered in a single composition. In one embodiment, Compound 1 or a pharmaceutically acceptable salt thereof and the other agent(s) are admixed in the composition.

In one embodiment, Compound 1 or a pharmaceutically acceptable salt thereof, is useful for treating pain, including chronic and acute pain. For example, Compound 1 or a pharmaceutically acceptable salt thereof, is useful in the treatment of multiple types of pain including inflammatory pain, neuropathic pain, back pain, and pain associated with cancer, surgery or bone fracture.

In one embodiment, Compound 1 or a pharmaceutically acceptable salt thereof, is useful for treating acute pain. Acute pain, as defined by the International Association for the Study of Pain, results from disease, inflammation, or injury to tissues. This type of pain generally comes on suddenly, for example, after trauma or surgery, and may be accompanied by anxiety or stress, and is confined to a given period of time and severity. In some instances, it can become chronic.

In one embodiment, Compound 1 or a pharmaceutically acceptable salt thereof, is useful for treating chronic pain. Chronic pain, as defined by the International Association for the Study of Pain, is widely believed to represent a disease in itself. It can be made much worse by environmental and psychological factors. Chronic pain persists over a longer period than acute pain and is resistant to most medical treatments, generally over 3 months or more. It can and often does cause severe problems for patients.

Accordingly, provided herein is a method of treating pain in a mammal, comprising administering to said mammal in need thereof Compound 1 or a pharmaceutically acceptable salt thereof, in an amount effective to treat said pain. In one embodiment, the pain is acute pain. In one embodiment, the pain is chronic pain. In one embodiment, the pain is chronic back pain. In one embodiment, the pain is neuropathic pain, such as pain associated with diabetic peripheral neuropathy or non-diabetic (e.g., chemotherapy induced) peripheral neuropathy. In one embodiment, the pain is inflammatory pain, such as pain associated with osteoarthritis. In one embodiment, the pain is pain associated with cancer. In one embodiment, the pain is pain associated with surgery. In one embodiment, the pain is pain associated with bone fracture.

Also provided herein is a method of preventing pain in a mammal, comprising administering to said mammal in need thereof Compound 1 or a pharmaceutically acceptable salt thereof, in an amount effective to prevent said pain. In one embodiment, the pain is acute pain. In one embodiment, the pain is chronic pain. In one embodiment, the pain is chronic back pain. In one embodiment, the pain is neuropathic pain, such as pain associated with diabetic peripheral neuropathy or non-diabetic (e.g., chemotherapy induced) peripheral neuropathy. In one embodiment, the pain is inflammatory pain, such as pain associated with osteoarthritis. In one embodiment, the pain is pain associated with cancer. In one embodiment, the pain is pain associated with surgery. In one embodiment, the pain is pain associated with bone fracture.

Also provided herein is a method of treating pain in a mammal, comprising co-administering to a mammal in need thereof an effective amount of: (a) Compound 1 or a pharmaceutically acceptable salt thereof; and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), opioids (such as morphine), calcitonin gene-related peptide receptor antagonists, subtype-selective ion channel modulators, anticonvulsants (for example pregabalin and gabapentin), dual serotonin-norepinephrine reuptake inhibitors (for example duloxetine, venlafaxine and milnacipran), JAK family kinase inhibitors (e.g., ruxolitinib or tofacitinib), and tricyclic antidepressants (such as amitriptyline, nortriptyline and desipramine). These additional therapeutic agents may be administered with Compound 1 or a pharmaceutically acceptable salt thereof as part of the same or separate dosage forms, via the same or different routes of administration, and on the same or different administration schedules according to standard pharmaceutical practice known to one skilled in the art.

Accordingly, also provided herein is a pharmaceutical combination comprising an effective amount of: (a) Compound 1 or a pharmaceutically acceptable salt thereof and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), for use in the treatment of pain in a mammal, wherein (a) and (b) can be in separate dosage forms or in the same dosage form. In one embodiment, provided herein is a pharmaceutical combination comprising (a) an effective amount of Compound 1 or a pharmaceutically acceptable salt thereof and (b) an effective amount of an analgesic such as an NSAID (e.g., aspirin, ibuprofen, indomethacin, and ketoprofen).

Compound 1 or a pharmaceutically acceptable salt thereof, is also useful for treating cancer. Particular examples include neuroblastoma, ovarian, pancreatic, colorectal and prostate cancer.

Accordingly, also provided herein is a method of treating cancer in a mammal, comprising administering to said mammal in need thereof Compound 1 or a pharmaceutically acceptable salt thereof, in an amount effective to treat said cancer.

Compound 1 or a pharmaceutically acceptable salt thereof, is also useful for treating a cancer having a dysregulation of TrkA.

Accordingly, also provided herein is a method for treating a patient diagnosed with a cancer having a dysregulation of TrkA, comprising administering to the patient a therapeutically effective amount of Compound 1 or a pharmaceutically acceptable salt thereof.

In one embodiment, the dysregulation of TrkA comprises overexpression of wild-type TrkA (autocrine/paracrine activation).

In one embodiment, the dysregulation of TrkA comprises gene amplification or one or more chromosome translocations or inversions resulting in TrkA gene fusions. In one embodiment, the dysregulation is a result of genetic translocations in which the expressed protein is a fusion protein containing residues from non-TrkA and TrkA proteins, and at a minimum the TrkA kinase domain. In one embodiment, the TrkA fusion protein is LMNA-TrkA, TFG-TrkA, TPM3-TrkA, CD74-TrkA, NFASC-TrkA, MPRIP-TrkA, BCAN-TrkA, or TPR-TrkA. In one embodiment the TrkA fusion protein is LMNA-TrkA, TFG-TrkA, TPM3-TrkA, CD74-TrkA, NFASC-TrkA, MPRIP-TrkA, BCAN-TrkA, TP53-TrkA, RNF213-TrkA, RABGAP1L-TrkA, IRF2BP2-TrkA, SQSTM1-TrkA, SSBP2-TrkA, or TPR-TrkA, where:

| | |
|---|---|
| LMNA = | Prelamin-A/C; |
| TFG = | TRK-fused gene protein; |
| TPM3 = | Tropomysin alpha-3; |
| CD74 = | HLA class II histocompatibility antigen gamma chain; |
| NFASC = | Neurofascin; |
| MPRIP = | MPRIP protein; |
| BCAN = | Brevican core protein; and |
| TP53 = | Cellular tumor antigen p53 |
| RNF213 = | E3 ubiquitin-protein ligase RNF213 |
| RABGAP1L = | Rab GTPase-activating protein 1-like |
| IRF2BP2 = | Interferon regulatory factor 2-binding protein 2 |
| SQSTM1 = | Sequestosome-1 |
| SSBP2 = | Single-stranded DNA-binding protein 2 |
| TPR = | Nucleoprotein TPR |

In one embodiment, the dysregulation of TrkA comprises one or more deletions, insertions or mutations in the TrkA protein. In one embodiment, the dysregulation comprises a deletion of one or more residues from the TrkA protein, resulting in constitutive activity of TrkA kinase. In one embodiment the deletion includes deletion of residues 303-377 in TrkA Isoform 2.

In one embodiment, the dysregulation of TrkA comprises a splice variation in which the expressed protein is an alternatively spliced variant of TrkA having one or more residues deleted resulting in constitutive activity of TrkA kinase. In one embodiment, an alternatively spliced form of TrkA with constitutive activity has deletions of exons 8, 9, and 11 resulting in an expressed protein missing residues 192-284 and 393-398 relative to TrkA Isoform 2.

Cancers identified as having dysregulation of TrkA (see literature references below; also see www.cancer.gov and www.nccn.org) include:

(A) Cancers wherein the dysregulation of TrkA comprises gene amplification or one or more chromosome translocations or inversions resulting in TrkA gene fusions, including:

| Cancer | Literature reference(s) | Standard of Care |
|---|---|---|
| Non-Small Cell Lung Cancer | Vaishnavi et al., *Nature Medicine*, 19, 1469-1472 (2013) | radiotherapy (e.g. radioiodide therapy, external-beam radiation, radium 223 therapy), chemotherapeutics as single agents (e.g. afatinib dimaleate, bevacizumab, carboplatin, cetuximab, cisplatin, crizotinib, erlotinib, gefitinib, gemcitabine, methotrexate, paclitaxel, pemetrexed) or combinations (e.g. carboplatin-paclitaxel, gemcitabine-paclitaxel, chemoradiation) |
| Papillary Thyroid Carcinoma | Caria P., et al., *Cancer Genetics and Cytogenetics*, 203: 21-29 (2010) | Radiotherapies (e.g. radioiodide therapy, external-beam radiation) and chemotherapeutics (e.g. sorafenib, sunitinib, pazopanib) |
| Glio-blastoma Multiforme | Frattini, V. et al., *Nature Genet.*, 45(10): 1141-1149 (2013) | Chemotherapeutics (e.g. bevacizumab, everolimus, lomustine, temozolomide) |

-continued

| Cancer | Literature reference(s) | Standard of Care |
|---|---|---|
| Colorectal Carcinoma | Martin-Zanca, D. et al., *Nature*, 319: 743-748 (1986) | Chemotherapeutics as single agents (aflibercept, bevacizumab, capecitabine, cetuximab, fluorouracil, irinotecan, leucovorin, oxaliplatin, panitumumab, regorafenib) or combinations (e.g. folfox, folfiri, capox, folfiri-bevacizumab, folfiri-cetuximab, xelox) |
| Melanoma | WO 2013/059740 A1 | Chemotherapeutics (e.g. aldesleukin, dabrafenib, dacarbazine, interferon alfa-2b, ipilimumab, peginterferon alfa-2b, trametinib, vemurafenib) |
| Cholangio-carcinoma | Ross, J. S. et al., *Oncologist*, 19, 235-242 (2014) | Chemotherapeutics (e.g. gemcitabine/cisplatin, fluoropyrimidines) |
| Sarcoma | Stransky, N. et al., *Nat. Comm.*, September 2014, 1-10 | Radiation therapy, chemotherapeutics (e.g. doxorubicin, ifosfamide, epirubicin, gemcitabine, dacarbazine, temozolomide, vinorelbine, pazopanib) |

(B) Cancers wherein the dysregulation of TrkA comprises one or more deletions, insertions or mutations in the TrkA protein, including:

| Cancer | Literature reference(s) | Standard of care |
|---|---|---|
| Acute Myeloid leukemia | Meyer, J. et al., *Leukemia* 21: 2171-2180 (2007); Reuther et al., *Mol. Cell Biol.* 20: 8655-8666 (2000) | Chemotherapeutics as single agents (e.g. arsenic trioxide, cyclophosphamide, cytarabine, daunorubicin, doxorubicin, vincristine) or combinations (e.g. ADE) |
| Large Cell Neuro-endocrine Carcinoma | Marchetti et al., *Human Mutation* 29(5): 609-616 (2008) | Radiotherapy (e.g. radioiodide therapy, external-beam radiation, radium 223 therapy) and/or chemotherapeutics (e.g. cisplatin, carboplatin, etoposide) |
| Neuro-blastoma | Tacconelli et al., *Cancer Cell* 6: 347-360 (2004) | Chemotherapeutics (e.g. cyclophosphamide, doxorubicin, vincristine) |

(C) Cancers driven by overexpression of wild-type TrkA (autocrine activation), including:

| Cancer | Literature Reference(s) | Standard of care |
|---|---|---|
| Prostate Carcinoma | Walch, E. T., et al., *Clinical & Experimental Metastasis* 17: 307-314 (1999); Papatsoris, A. G., et al., *Expert Opinion on Investigational Drugs* 16(3): 303-309 (2007) | Radiotherapy (e.g. radium 223 therapy) or chemotherapeutics (e.g. abiraterone, cabazitaxel, degarelix, denosumab, docetaxel, enzalutamide, leuprolide, prednisone, sipuleucel-T) |
| Neuro-blastoma | Van Noesel, M. M. et al., *Gene* 325: 1-15 (2004) | Chemotherapeutics (e.g. cyclophosphamide, doxorubicin, vincristine) |

-continued

| Cancer | Literature Reference(s) | Standard of care |
|---|---|---|
| Pancreatic Carcinoma | Zhang, Y., et al., *Oncology Reports* 14: 161-171 (2005) | Chemotherapeutics as single agents (e.g. erlotinib, fluorouracil, gemcitabine, mitomycin C) or combinations (e.g. gemcitabine-oxaliplatin) |
| Melanoma | Truzzi, F., et al., *Journal of Investigative Dermatology* 128(8): 2031-2040 (2008) | Chemotherapeutics (e.g. aldesleukin, dabrafenib, dacarbazine, interferon alfa-2b, ipilimumab, peginterferon alfa-2b, trametinib, vemurafenib) |
| Head and Neck Squamous Cell Carcinoma | Kolokythas, D., et al., *Journal of Oral and Maxillofacial Surgery* 68(6): 1290-1295 (2010) | Radiotherapy and/or Chemotherapeutics (e.g. bleomycin, cetuximab, cisplatin, docetaxel, fluorouracil, methotrexate) |
| Gastric Carcinoma | Ni, S-Z., et al., *Asian Pacific Journal of Cancer Prevention* 13: 1511-1514 (2012) | Chemotherapeutics (e.g. docetaxel, doxorubicin, fluorouracil, mitomycin C, trastuzumab) |

In one embodiment, provided herein is a method for treating a patient diagnosed with a cancer having a dysregulation of TrkA, comprising administering to the patient Compound 1 or a pharmaceutically acceptable salt thereof in an amount effective to treat said cancer, wherein the cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma. In one embodiment, provided herein is a method for treating a patient diagnosed with a cancer having a dysregulation of TrkA, comprising administering to the patient Compound 1 or a pharmaceutically acceptable salt thereof in an amount effective to treat said cancer, wherein the cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma, gastric carcinoma, cholangiocarcinoma and sarcoma.

Also provided is a method for treating cancer in a mammal in need thereof, the method comprising: (a) determining if the cancer is associated with a dysregulation of TrkA kinase; and (b) if the cancer is determined to be associated with a dysregulation of TrkA kinase, administering to the mammal a therapeutically effective amount of compound 1 or a pharmaceutically acceptable salt thereof. In one embodiment, Compound 1 is a dihydrochloride salt.

In one embodiment, the dysregulation of TrkA comprises one or more chromosome translocations or inversions resulting in TrkA gene fusions. In one embodiment, the TrkA gene fusion is LMNA-TrkA, TFG-TrkA, TPM3-TrkA, CD74-TrkA, NFASC-TrkA, MPRIP-TrkA, BCAN-TrkA, TP53-TrkA, RNF213-TrkA, RABGAP1L-TrkA, IRF2BP2-TrkA, SQSTM1-TrkA, SSBP2-TrkA, or TPR-TrkA. In one embodiment, the cancer is non-small cell lung cancer, papillary thyroid carcinoma, glioblastoma multiforme, colorectal carcinoma, melanoma, cholangiocarcinoma, or sarcoma.

In one embodiment, the dysregulation of TrkA comprises one or more deletions, insertions or mutations in the TrkA protein. In one embodiment, the cancer is acute myeloid leukemia, large cell neuroendocrine carcinoma, or neuroblastoma.

In one embodiment, the dysregulation of TrkA is overexpression of wild-type TrkA (autocrine activation). In one embodiment, the cancer is prostate carcinoma, neuroblastoma, pancreatic carcinoma, melanoma, head and neck squamous cell carcinoma, or gastric carcinoma.

In one embodiment, any of the above methods method for treating cancer in a mammal in need thereof further comprises administering an effective amount of Compound 1 or a pharmaceutically acceptable salt thereof in combination with an effective amount of at least one additional therapeutic agent selected from one or more additional therapy or chemotherapeutic agent.

In one embodiment, any of the above methods method for treating cancer in a mammal in need thereof comprises administering to said mammal in need thereof an effective amount of Compound 1 or a pharmaceutically acceptable salt thereof in combination with one or more additional chemotherapeutic agents.

In one embodiment, the additional chemotherapeutic agent(s) is selected from receptor tyrosine kinase-targeted therapeutic agents, including cabozantinib, crizotinib, erlotinib, gefitinib, imatinib, lapatinib, nilotinib, pazopanib, pertuzumab, regorafenib, sunitinib, and trastuzumab.

In one embodiment, the additional chemotherapeutic agent(s) is selected from signal transduction pathway inhibitors, including Ras-Raf-MEK-ERK pathway inhibitors (e.g. binimetinib, selumetinib, encorafinib, sorafenib, trametinib, vemurafenib), PI3K-Akt-mTOR-S6K pathway inhibitors (e.g. everolimus, rapamycin, perifosine, temsirolimus) and modulators of the apoptosis pathway (e.g. obataclax).

In one embodiment, the additional chemotherapeutic agent(s) is selected from cytotoxic chemotherapeutics, including arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

In one embodiment, the additional chemotherapeutic agent(s) is selected from angiogenesis-targeted therapies, including aflibercept and bevacizumab.

In one embodiment, the additional chemotherapeutic agent(s) is selected from immune-targeted agents, including aldesleukin, ipilimumab, lambrolizumab, nivolumab, sipuleucel-T.

In one embodiment, the additional chemotherapeutic agent(s) is selected from agents active against the TrkA pathway, including NGF-targeted biopharmaceuticals such as NGF antibodies, and panTrk inhibitors.

In one embodiment, the additional therapeutic agent or therapy is radiotherapy, including radioiodide therapy, external-beam radiation and radium 223 therapy.

In one embodiment, the additional therapeutic agent(s) includes any one of the above listed therapies or therapeutic agents which are standards of care in cancers wherein the cancer has a dysregulation of TrkA.

In one embodiment, provided herein is a method of treating cancer in a patient in need thereof, comprising administering to said patient Compound 1 or a pharmaceutically acceptable salt thereof, in combination with at least one additional therapy or chemotherapeutic agent selected from radiotherapy (e.g. radioiodide therapy, external-beam radiation, radium 223 therapy), cytotoxic chemotherapeutics (e.g. arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, vincristine), tyrosine kinase targeted-therapeutics (e.g. afatinib, cabozantinib, cetuximab, crizotinib, dabrafenib, erlotinib, gefitinib, imatinib, lapatinib, nilotinib, pazopanib, panitumumab, pertuzumab, regorafenib, sunitinib, trastuzumab), apoptosis modulators and signal transduction inhibitors (e.g. everolimus, perifosine, rapamycin, binimetinib, selumetinib, encorafinib, sorafenib, temsirolimus, trametinib, vemurafenib), immune-targeted therapies (e.g. aldesleukin, interferon alfa-2b, ipilimumab, lambrolizumab, nivolumab, prednisone, sipuleucel-T) and angiogenesis-targeted therapies (e.g. aflibercept, bevacizumab), wherein the amount of Compound 1 or a pharmaceutically acceptable salt thereof is, in combination with the additional therapy or therapeutic agent, effective in treating said cancer. These additional therapeutic agents may be administered with Compound 1 or a pharmaceutically acceptable salt thereof as part of the same or separate dosage forms, via the same or different routes of administration, and on the same or different administration schedules according to standard pharmaceutical practice known to one skilled in the art.

Also provided herein is (i) a pharmaceutical combination for treating cancer in a patient in need thereof, which comprises (a) Compound 1 or a pharmaceutically acceptable salt thereof, (b) an additional therapeutic agent and (c) optionally at least one pharmaceutically acceptable carrier for simultaneous, separate or sequential use for the treatment of cancer, wherein the amounts of Compound 1 or a pharmaceutically acceptable salt thereof and of the additional therapeutic agent are together effective in treating said cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer a patient in need thereof.

In one embodiment, the combination therapy is for treating a cancer selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma. In one embodiment, the combination therapy is for treating a cancer selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma, gastric carcinoma, cholangiocarcinoma and sarcoma.

Compound 1, or a pharmaceutically acceptable salt thereof, is also useful for treating inflammation or an inflammatory disease or disorder.

Accordingly, provided herein is a method of treating inflammation or an inflammatory disease or disorder in a mammal, comprising administering to said mammal in need thereof Compound 1 or a pharmaceutically acceptable salt thereof in an amount effective to treat said inflammation. In one embodiment, the inflammatory disease is selected from inflammatory lung diseases (such as asthma), interstitial cystitis (IC), painful bladder syndrome (PBS), inflammatory bowel diseases (including ulcerative colitis and Crohn's disease), and inflammatory skin diseases such as atopic dermatitis and psoriasis.

In one embodiment, the method of treating inflammation or an inflammatory disease or disorder comprises administering to a mammal in need thereof Compound 1 or a pharmaceutically acceptable salt thereof in combination with one or more additional agents. Examples of additional agents include anti-TNF agents (for example monoclonal antibody such as infliximab (Remicade), adalimumab (Humira), certolizumab pegol (Cimzia), and golimumab (Simponi), or a circulating receptor fusion protein such as etanercept (Enbrel)), antimetabolite and antifolate drugs (for example Methotrexate), or targeted kinase inhibitors (for example JAK family inhibitors such as Ruxolitinib, Tofacitinib, CYT387, Lestaurtinib, Pacritinib and TG101348). These additional therapeutic agents may be administered with Compound 1 or a pharmaceutically acceptable salt thereof as part of the same or separate dosage forms, via the same or different routes of administration, and on the same or different administration schedules according to standard pharmaceutical practice known to one skilled in the art.

Compound 1 or a pharmaceutically acceptable salt thereof, is also useful for treating a neurodegenerative disease in a mammal. In one embodiment, Compound 1 or a pharmaceutically acceptable salt thereof may also be used to treat demyelination and dysmyelination by promoting myelination, neuronal survival, and oligodendrocyte differentiation via blocking Sp35-TrkA interaction.

Accordingly, also provided herein is a method of treating a neurodegenerative disease in a mammal, comprising administering to said mammal in need thereof Compound 1 or a pharmaceutically acceptable salt thereof in an amount effective to treat said neurodegenerative disease. In one embodiment, the neurodegenerative disease is multiple sclerosis. In one embodiment, the neurodegenerative disease is Parkinson's disease. In one embodiment, the neurodegenerative disease is Alzheimer's disease.

Also provided herein is a method of treating certain infectious diseases such as *Trypanosoma cruzi* infection in a mammal, comprising administering to said mammal in need thereof Compound 1 or a pharmaceutically acceptable salt thereof in an amount effective to treat said *Trypanosoma cruzi* infection.

Also provided herein is a method of treating Sjogren's syndrome in a mammal, comprising administering to said mammal in need thereof Compound 1 or a pharmaceutically acceptable salt thereof in an amount effective to treat said syndrome.

Also provided herein is a method of treating endometriosis in a mammal, comprising administering to said mammal in need thereof Compound 1 or a pharmaceutically acceptable salt thereof in an amount effective to treat said endometriosis.

Also provided herein is a method of treating diabetic peripheral neuropathy in a mammal, comprising administering to said mammal in need thereof Compound 1 or a pharmaceutically acceptable salt thereof in an amount effective to treat said diabetic peripheral neuropathy.

Also provided herein is a method of treating prostatitis in a mammal, comprising administering to said mammal in need thereof Compound 1 or a pharmaceutically acceptable salt thereof in an amount effective to treat said prostatitis.

Also provided herein is a method of treating pelvic pain syndrome in a mammal, comprising administering to said mammal in need thereof Compound 1 or a pharmaceutically acceptable salt thereof in an amount effective to treat said pelvic pain syndrome.

Also provided herein is a method of treating diseases related to an imbalance of the regulation of bone remodeling in a mammal, comprising administering to said mammal in need thereof Compound 1 or a pharmaceutically acceptable salt thereof in an amount effective to treat said disease. In one embodiment, the disease is osteoporosis, rheumatoid arthritis, or bone metastases.

In one embodiment, the method for treating diseases related to an imbalance of the regulation of bone remodeling in a mammal in need thereof comprises administering Compound 1 or a pharmaceutically acceptable salt thereof in combination with one or more additional therapeutic agents or therapies. Examples of additional therapeutic agents or therapies include anti-TNF treatments (for example monoclonal antibody such as infliximab (Remicade), adalimumab (Humira), certolizumab pegol (Cimzia), and golimumab (Simponi), or with a circulating receptor fusion protein such as etanercept (Enbrel)), antimetabolite and antifolate drug (for example Methotrexate), or targeted kinase inhibitors (for example JAK family inhibitors Ruxolitinib, Tofacitinib, CYT387, Lestaurtinib, Pacritinib and TG101348). These additional therapeutic agents may be administered with Compound 1 or a pharmaceutically acceptable salt thereof as part of the same or separate dosage forms, via the same or different routes of administration, and on the same or different administration schedules according to standard pharmaceutical practice known to one skilled in the art.

Also provided herein is a method of treating diseases resulting from Connective Tissue Growth Factor aberrant signaling in a mammal in need thereof, comprising administering to said mammal Compound 1 or a pharmaceutically acceptable salt thereof in an amount effective to treat said disease. In one embodiment, the disease resulting from Connective Tissue Growth Factor aberrant signaling is Raynaud's Syndrome, Idiopathic pulmonary fibrosis, scarring (hypertrophic, keloid and others), cirrhosis, endomyocardial fibrosis, atrial fibrosis, myelofibrosis, progressive massive fibrosis (lung), nephrogenic systemic fibrosis, scleroderma, systemic sclerosis, arthrofibrosis or ocular fibrosis.

As used herein, an "effective amount" means an amount of compound that, when administered to a mammal in need of such treatment, is sufficient to (i) treat a particular disease, condition, or disorder which can be treated with Compound 1 or a pharmaceutically acceptable salt thereof, or (ii) attenuate, ameliorate, or eliminate one or more symptoms of the particular disease, condition, or disorder described herein. The amount of Compound 1 that will correspond to such an amount will vary depending upon factors such as the disease condition and its severity, and the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

Compound 1 or a pharmaceutically acceptable salt thereof may be administered by any convenient route, e.g. into the gastrointestinal tract (e.g. rectally or orally), the nose, lungs, musculature or vasculature, wound irrigation, or transdermally or dermally. Compound 1 or a pharmaceutically acceptable salt thereof may be administered in any convenient administrative form, e.g. tablets, powders, capsules, solutions, dispersions, suspensions, syrups, sprays, suppositories, gels, emulsions, patches, etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

Another formulation may be prepared by mixing Compound 1 or a pharmaceutically acceptable salt thereof and a carrier or excipient. Suitable carriers and excipients are well known to those skilled in the art. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

Accordingly, also provided herein is a pharmaceutical composition, which comprises Compound 1 or a pharmaceutically acceptable salt thereof together with a pharmaceutically acceptable diluent or carrier. In one embodiment, a pharmaceutical composition comprising Compound 1 or a pharmaceutically acceptable salt thereof is formulated for oral administration. In one embodiment, a pharmaceutical composition comprising Compound 1 or a pharmaceutically acceptable salt thereof formulated for oral administration is in the form of a tablet or capsule.

Also provided herein is Compound 1 or a pharmaceutically acceptable salt thereof for use in the treatment of pain in a mammal. In one embodiment, the pain is chronic pain. In one embodiment the pain is acute pain. In one embodiment, the pain is chronic back pain, inflammatory pain, neuropathic pain, or pain associated with cancer, surgery, or bone fracture.

Also provided herein is Compound 1 or a pharmaceutically acceptable salt thereof for use in the treatment of cancer in a mammal. In one embodiment, the cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma, gastric carcinoma, cholangiocarcinoma and sarcoma.

Also provided herein is Compound 1 or a pharmaceutically acceptable salt thereof for use in the treatment of inflammation or an inflammatory disease or disorder in a mammal. In one embodiment, the inflammatory disease is inflammatory lung diseases (such as asthma), interstitial cystitis, bladder pain syndrome, inflammatory bowel diseases (including ulcerative colitis and Crohn's disease), and inflammatory skin diseases such as atopic dermatitis.

Also provided herein is Compound 1 or a pharmaceutically acceptable salt thereof for use in the treatment of infectious diseases, for example *Trypanosoma cruzi* infection, in a mammal.

Also provided herein is Compound 1 or a pharmaceutically acceptable salt thereof for use in the treatment of Sjogren's syndrome in a mammal.

Also provided herein is Compound 1 or a pharmaceutically acceptable salt thereof for use in the treatment of endometriosis in a mammal.

Also provided herein is Compound 1 or a pharmaceutically acceptable salt thereof for use in the treatment of diabetic peripheral neuropathy in a mammal.

Also provided herein is Compound 1 or a pharmaceutically acceptable salt thereof for use in the treatment of prostatitis in a mammal.

Also provided herein is Compound 1 or a pharmaceutically acceptable salt thereof for use in the treatment of pelvic pain syndrome in a mammal.

Also provided herein is Compound 1 or a pharmaceutically acceptable salt thereof for use in the treatment of a neurodegenerative disease in a mammal.

Also provided herein is Compound 1 or a pharmaceutically acceptable salt thereof for use in the treatment of a disease related to an imbalance of the regulation of bone remodeling.

Also provided herein is Compound 1 or a pharmaceutically acceptable salt thereof for use in the treatment of diseases resulting from Connective Tissue Growth Factor aberrant signaling.

Also provided herein is the use of Compound 1 or a pharmaceutically acceptable salt thereof in the manufacture of a medicament for the treatment of a condition selected from pain, cancer, inflammation, neurodegenerative disease, *Trypanosoma cruzi* infection, and diseases resulting from Connective Tissue Growth Factor aberrant signaling. In one embodiment, the condition is chronic pain. In one embodiment, the condition is acute pain. In one embodiment, the pain is chronic back pain. In one embodiment, the pain is inflammatory pain, neuropathic pain, or pain associated with cancer, surgery, or bone fracture. In one embodiment, the condition is cancer. In one embodiment, the condition is inflammation. In one embodiment, the condition is a neurodegenerative disease. In one embodiment, the condition is *Trypanosoma cruzi* infection. In one embodiment, the condition is Sjogren's syndrome. In one embodiment, the condition is endometriosis. In one embodiment, the condition is diabetic peripheral neuropathy. In one embodiment, the condition is prostatitis. In one embodiment, the condition is pelvic pain syndrome. In one embodiment, the disease is a disease related to an imbalance of the regulation of bone remodeling. In one embodiment, the disease is a disease resulting from Connective Tissue Growth Factor aberrant signaling.

Also provided herein is a medicament comprising Compound 1 or a pharmaceutically acceptable salt thereof for treatment of pain in a mammal in combination with an additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), opioids (such as morphine), calcitonin gene-related peptide receptor antagonists, subtype-selective ion channel modulators, anticonvulsants (for example Pregabalin and gabapentin), dual serotonin-norepinephrine reuptake inhibitors (for example duloxetine, venlafaxine and milnacipran), JAK family kinase inhibitor (such as ruxolitinib or tofacitinib), and tricyclic antidepressants (such as amitriptyline, nortriptyline and desipramine). In one embodiment, provided herein is a medicament comprising Compound 1 or a pharmaceutically acceptable salt thereof for treatment of pain in a mammal in combination with an NSAID.

Also provided herein is a medicament comprising a therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine) for treatment of pain in a mammal in combination with Compound 1 or a pharmaceutically acceptable salt thereof.

EXAMPLES

Preparation of Synthetic Intermediates

Preparation A

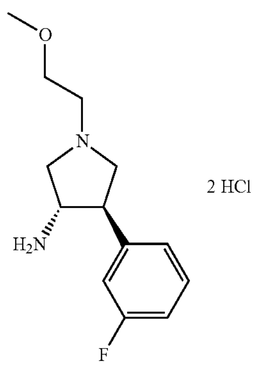 [SMILES: COCCN1C[C@@H](N)[C@H](c2cccc(F)c2)C1]

(3S,4R)-4-(3-fluorophenyl)-1-(2-methoxyethyl)pyrrolidin-3-amine dihydrochloride

Step A: Preparation of tert-butyl (3S,4R)-4-(3-fluorophenyl)-1-(2-methoxyethyl)pyrrolidin-3-ylcarbamate: A solution of tert-butyl (3S,4R)-4-(3-fluorophenyl)pyrrolidin-3-ylcarbamate (250 mg, 0.89 mmol, commercially available), DIEA (0.48 mL, 2.68 mmol) and 1-bromo-2-methoxyethane (149 mg, 1.07 mmol) in DMF (3 mL) was stirred at ambient temperature for 2 hours, then heated to 60° C. for 4 hours, then cooled to ambient temperature over 16 hours. After partitioning between EtOAc and saturated $NaHCO_3$ (10 mL each), the organic layer was washed with water and brine (2×10 mL each), dried over $Na_2SO_4$, filtered and concentrated to yield tert-butyl (3S,4R)-4-(3-fluorophenyl)-1-(2-methoxyethyl)pyrrolidin-3-ylcarbamate (250 mg, 83% yield) as a viscous orange oil. LCMS (apci) m/z=339.1 (M+H).

Step B: Preparation of (3S,4R)-4-(3-fluorophenyl)-1-(2-methoxyethyl)pyrrolidin-3-amine dihydrochloride: A solution of tert-butyl (3S,4R)-4-(3-fluorophenyl)-1-(2-methoxyethyl)pyrrolidin-3-ylcarbamate (250 mg, 0.74 mmol) in 5-6 N HCl in isopropyl alcohol (14.8 mL, 73.9 mmol) was stirred at ambient temperature for 1 hour. The mixture was concentrated under vacuum and triturated with $Et_2O$ to afford the title compound (230 mg, 100% yield) as a beige solid. LCMS (apci) m/z=239.1 (M+H).

Preparation B 4-methyl-3-(2-methylpyrimidin-5-yl)-1-phenyl-1H-pyrazol-5-amine Step A: Preparation of 5-amino-4-methyl-1-phenyl-1H-pyrazol-3(2H)-one: A mixture of ethyl 2-cyanopropanoate (50.5 g, 397.2 mmol) and phenylhydrazine (39 mL, 397.2 mmol) in dioxane (100 mL) was heated at 110° C. for 5 days. The cooled mixture was concentrated to ½ volume and then cooled in ice and triturated with cold $Et_2O$. The resulting solids were filtered, washed extensively with $Et_2O$ and dried under vacuum to afford 5-amino-4-methyl-1-phenyl-1H-pyrazol-3(2H)-one (34.69 g, 46% yield) as a fluffy white powder. MS (apci) m/z=190.1 (M+H).

Step B: Preparation of 5-amino-4-methyl-1-phenyl-1H-pyrazol-3-yl trifluoromethane sulfonate: A suspension of 5-amino-4-methyl-1-phenyl-1H-pyrazol-3(2H)-one (13.72 g, 72.5 mmol) and N-phenylbis(trifluoromethylsulfonamide) (27.2 g, 76.1 mmol) in DMF (100 mL) was treated with DIEA (37.9 mL, 217.5 mmol) and the mixture stirred at ambient temperature for 16 hours. The mixture was partitioned between saturated $NaHCO_3$ (400 mL) and EtOAc (200 mL) and the aqueous layer was extracted with EtOAc (2×200 mL). The combined organic phases were washed with water (5×50 mL) and brine (50 mL), then dried over $Na_2SO_4$, filtered and concentrated under vacuum. The residue was purified by silica column chromatography eluting with 4:1 hexanes/EtOAc, to afford 5-amino-4-methyl-1-phenyl-1H-pyrazol-3-yl trifluoromethane sulfonate (23.1 g, 99% yield) as a pale yellow solid. MS (apci) m/z=322.0 (M+H).

Step C: Preparation of 4-methyl-3-(2-methylpyrimidin-5-yl)-1-phenyl-1H-pyrazol-5-amine: 5-Amino-4-methyl-1-phenyl-1H-pyrazol-3-yl trifluoromethane sulfonate (900 mg, 2.8 mmol), 2-methyl-5-(4,4,5,5-tetramethyl-1,3,2-dioxaborolan-2-yl)pyrimidine (925 mg, 4.2 mmol), $K_2CO_3$ (1.55 g, 11.2 mmol) and $Pd(PPh_3)_4$ (324 mg, 0.28 mmol) were combined in toluene (10 mL), water (5 mL) and EtOH (2.5 mL) and warmed to 95° C. in a sealed tube for 16 hours. The cooled mixture was filtered and the filtrate was partitioned between water (50 mL) and EtOAc (50 mL). The aqueous layer was extracted with EtOAc (2×30 mL) and the combined organic phases were washed with brine (30 mL), dried over $Na_2SO_4$, filtered and concentrated under vacuum. The residue was purified by silica column chromatography, eluting with 2% MeOH/DCM, to afford the title compound (533 mg, 72% yield) as a pink solid. MS (apci) m/z=266.1 (M+H).

Preparation C

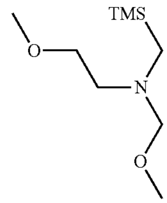

2-methoxy-N-(methoxymethyl)-N-((trimethylsilyl)methyl)ethanamine

Step A: Preparation of 2-methoxy-N-((trimethylsilyl)methyl)ethanamine: To a DMSO solution (15 mL) of 2-methoxyethanamine (14.2 mL, 163 mmol) at 90° C. was added a DMSO (10 mL) solution of (chloromethyl)trimethylsilane (11.4 mL, 81.5 mmol) by addition funnel over 40 minutes. The mixture was heated at 90° C. for 3.5 hours then cooled to ambient temperature. The mixture was then diluted with $H_2O$ (150 mL) and extracted with EtOAc (2×150 mL). The combined organic extracts were washed with brine (150 mL), dried with $MgSO_4$, filtered and concentrated to afford 2-methoxy-N-((trimethylsilyl)methyl)ethanamine (8.14 g, 62% yield) as a yellow oil. MS (apci) m/z=162.0 (M+H).

Step B: Preparation of 2-methoxy-N-(methoxymethyl)-N-((trimethylsilyl)methyl)ethanamine: A MeOH (2.45 mL) solution of formaldehyde (37% aqueous, 4.91 g, 60.6 mmol) was cooled to 0° C., and treated with a dropwise addition of 2-methoxy-N-((trimethylsilyl)methyl)ethanamine (8.14 g, 50.5 mmol). The biphasic mixture was stirred at 0° C. for 3 hours, then $K_2CO_3$ (6.97 g, 50.5 mmol) was added and the mixture was stirred at 0° C. for 1 hour. The yellow oil was decanted onto $K_2CO_3$ (2.00 g, 14.4 mmol), and the mixture was stirred at ambient temperature for 2 hours. After the yellow oil was decanted, the solid $K_2CO_3$ was washed with $Et_2O$ (2×10 mL), and the $Et_2O$ washings were combined with the decanted yellow oil and concentrated on a rotary evaporator to yield the title compound (9.92 g, 96% yield) as a yellow oil. $^1H$ NMR ($CDCl_3$) δ 4.00 (s, 2H), 3.37-3.43 (m, 2H), 3.29 (s, 3H), 3.19 (s, 3H), 2.77-2.82 (m, 2H), 2.18 (s, 2H), 0.00 (s, 9H) ppm.

Preparation D

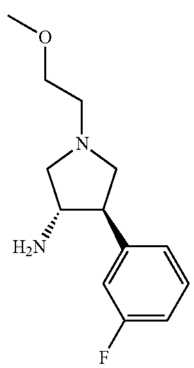 [SMILES: COCCN1C[C@@H](N)[C@H](c2cccc(F)c2)C1]

(3S,4R)-4-(3-fluorophenyl)-1-(2-methoxyethyl)pyrrolidin-3-amine

Step A: Preparation of (trans)-4-(3-fluorophenyl)-1-(2-methoxyethyl)pyrrolidine-3-carboxylic acid: (E)-3-(3-fluorophenyl)acrylic acid (25.20 g, 151.7 mmol) was treated sequentially with EtOAc (75 mL) and heptane (75 mL), followed by TFA (1.17 mL, 15.17 mmol). The mixture was placed in a cool-water bath (internal temperature 15° C.), and 2-methoxy-N-(methoxymethyl)-N-((trimethylsilyl)methyl)ethanamine [Preparation C] (69.82 g, 197.2 mmol) was added dropwise from an addition funnel over 20 minutes, adding ice to the water bath to maintain the internal temperature between 13-19° C. during the addition. The ice bath was removed and the mixture stirred at ambient temperature for 18 hours, then cooled (internal temperature 13° C.), and additional 2-methoxy-N-(methoxymethyl)-N-((trimethylsilyl)methyl)ethanamine (Preparation C; 34 g) was added dropwise from an addition funnel over 6 minutes. The bath was removed and after stirring for a further 4 hours at ambient temperature, the mixture was concentrated to half volume. Heptane (100 mL) was added and the mixture partially concentrated, removing about 150 mL solvent. This was repeated twice, removing 100 mL solvent each time. The residual slurry was rinsed into the bottom of the flask with heptane (50 mL) then was sealed and stirred at ambient temperature for 64 hours. Solids were filtered, rinsed with heptane (2×50 mL) and dried under vacuum to afford (trans)-4-(3-fluorophenyl)-1-(2-methoxyethyl)pyrrolidine-3-carboxylic acid (44.99 g, 111% yield) as a pale yellow solid which was used directly in the next step, assuming 100% yield. MS (apci) m/z=268.1 (M+H).

Step B: Preparation of (trans)-4-(3-fluorophenyl)-1-(2-methoxyethyl)pyrrolidine-3-carboxamide: To a suspension of (trans)-4-(3-fluorophenyl)-1-(2-methoxyethyl)pyrrolidine-3-carboxylic acid (40.54 g, 151.7 mmol) in THF (440 mL) were added CDI (31.97 g, 197.2 mmol) followed by imidazole hydrochloride (3.171 g, 30.33 mmol). The reaction mixture was stirred at ambient temperature for 16 hours, and ammonia (135.0 mL, 2M in iPrOH, 270.0 mmol) was then added by addition funnel over 30 minutes. After stirring for an additional 3 hours, the resulting solids were filtered, washed with EtOAc and the filtrate concentrated. The residue was dissolved in EtOAc (200 mL) and washed with 25/75 water:brine (2×200 mL). The organic phase was dried over $MgSO_4$, filtered, concentrated and dried under vacuum to afford (trans)-4-(3-fluorophenyl)-1-(2-methoxyethyl)pyrrolidine-3-carboxamide (54.97 g, 136% yield) as a yellow solid which was used assuming 100% yield. MS (apci) m/z=267.2 (M+H).

Step C: Preparation of (trans)-4-(3-fluorophenyl)-1-(2-methoxyethyl)pyrrolidin-3-amine: To a solution of (trans)-4-(3-fluorophenyl)-1-(2-methoxyethyl)pyrrolidine-3-carboxamide (29.33 g, 85.90 mmol) in MeOH (345 mL), in a 3-necked 1-L round bottomed flask, equipped with temperature probe, cooled in an ice bath, was added NaOCl (10-15% available Cl, aqueous solution) (116.3 mL, 189.0 mmol) from an addition funnel over 20 minutes [internal temperature was between 7-13° C.]. The ice bath was removed and the heterogeneous mixture was stirred at ambient temperature for 90 minutes, then at 55° C. for 3 hours. A solution of KOH (67.48 g, 1203 mmol) in $H_2O$ (225.9 mL, 12,542 mmol) was added and the solution was stirred at 75° C. for 19 hours. The mixture was cooled to 0° C., and concentrated HCl (147.1 mL, 4,802 mmol) was added slowly over 30 minutes. The pH was adjusted to 6 by addition of aqueous $K_3PO_4$ (30 wt %, 155 mL), and the mixture was partially concentrated to remove organic solvents. Aqueous $K_3PO_4$ (30 wt %, 280 mL) was added until pH 10, and the mixture was extracted with EtOAc (2×450 mL). The combined organic extracts were concentrated and dried under vacuum to afford (trans)-4-(3-fluorophenyl)-1-(2-methoxyethyl)pyrrolidin-3-amine (28.08 g, 91% yield) as a dark amber syrup. MS (apci) m/z=239.2 (M+H).

Step D: Preparation of (3S,4R)-4-(3-fluorophenyl)-1-(2-methoxyethyl)pyrrolidin-3-amine(2S,3S)-2,3-bis((4-methylbenzoyl)oxy)succinate: (trans)-4-(3-fluorophenyl)-1-(2-methoxyethyl)pyrrolidin-3-amine (125 mg, 0.52 mmol) and (2S,3S)-2,3-bis((4-methylbenzoyl)oxy)succinic acid (222.9 mg, 0.58 mmol) were weighed into a 4 mL vial, then treated with MeOH (1.57 mL) followed by water (0.175 mL). The vial was capped and the reaction mixture was stirred at 50° C. for 5 minutes, then allowed to cool slowly to ambient temperature over 17 hours. The resulting solids were filtered, washed with $Et_2O$ (4×0.2 mL) and dried under vacuum to afford (3S,4R)-4-(3-fluorophenyl)-1-(2-methoxyethyl)pyrrolidin-3-amine(2S,3S)-2,3-bis((4-methylbenzoyl)oxy)succinate (131.6 mg, 40% yield) as a white solid. Chiral SFC analysis of a free-based sample indicated >95% ee. This material was used as seed crystals in the following step:

(Trans)-4-(3-fluorophenyl)-1-(2-methoxyethyl)pyrrolidin-3-amine (7.39 g, 18.61 mmol) was dissolved in MeOH (52.7 mL) and treated with (2S,3S)-2,3-bis((4-methylbenzoyl)oxy)succinic acid (10.78 g, 27.91 mmol) followed by $H_2O$ (9.3 mL). The mixture was stirred at 50° C. for 5 minutes. Seed crystals (90 mg) were added to the solution, and the mixture was allowed to warm slowly to ambient temperature over 16 hours. The resulting solids were filtered, rinsed with $Et_2O$ (4×5 mL) and dried under vacuum. The residue was slurried in MeOH (15 mL) and $H_2O$ (2.7 mL), stirred at 50° C. for 15 minutes, then allowed to slowly cool to ambient temperature over 19 hours. The solids were filtered, washed with $Et_2O$ (3×5 mL) and dried under vacuum to afford (3S,4R)-4-(3-fluorophenyl)-1-(2-methoxyethyl)pyrrolidin-3-amine(2S,3S)-2,3-bis((4-methylbenzoyl)oxy)succinate (3.12 g, 27% yield) as a white solid. Chiral analysis on a free-based sample indicated >99.7% ee.

Step E: Preparation of (3S,4R)-4-(3-fluorophenyl)-1-(2-methoxyethyl)pyrrolidin-3-amine: A suspension of (3S,4R)-4-(3-fluorophenyl)-1-(2-methoxyethyl)pyrrolidin-3-amine (2S,3S)-2,3-bis((4-methylbenzoyl)oxy)succinate (2.89 g, 4.63 mmol) in DCM (25 mL) was washed with 1M aqueous NaOH (2×15 mL). The combined aqueous phases were extracted with DCM (25 mL), and the combined organic extracts were washed with brine (30 mL), dried over $Na_2SO_4$, filtered, concentrated and dried under vacuum to afford (3S,4R)-4-(3-fluorophenyl)-1-(2-methoxyethyl)pyrrolidin-3-amine (998 mg, 90% yield) as a light beige oil. MS (apci) m/z=239.2 (M+H).

SYNTHETIC EXAMPLES

Example 1

1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea dihydrochloride

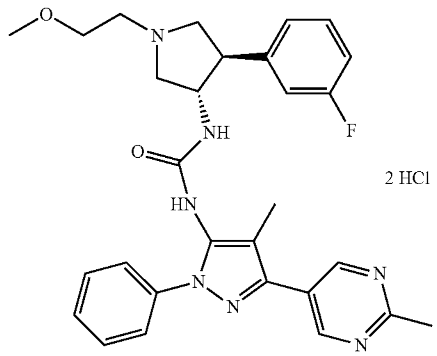

Step A: Preparation of 1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea: To a solution of 4-methyl-3-(2-methylpyrimidin-5-yl)-1-phenyl-1H-pyrazol-5-amine (Preparation B; 61 mg, 0.16 mmol) in DCM (2 mL) was added triphosgene (24 mg, 0.08 mmol) followed by DIEA (84 μL, 0.48 mmol). The mixture was stirred at ambient temperature for 15 minutes and then treated with (3S,4R)-4-(3-fluorophenyl)-1-(2-methoxyethyl)pyrrolidin-3-amine dihydrochloride (Preparation A; 50 mg, 0.16 mmol) and DIEA (84 μL, 0.48 mmol). The reaction mixture was stirred for 16 hours. The mixture was partitioned between water (10 mL) and DCM (10 mL) and the aqueous layer was extracted with DCM (2×10 mL). The combined organic phases were washed with brine (10 mL), dried over $Na_2SO_4$, filtered and concentrated. The residue was purified by silica column chromatography, eluting with 2.5-5% MeOH/DCM. Fractions containing the product were further purified by reverse phase HPLC (5-95% ACN/water/0.1% TFA) to afford the title compound after basic aqueous work-up (28 mg, 33% yield) as a white solid. MS (apci) m/z=530.3 (M+H).

Step B: Preparation of 1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea dihydrochloride: To a solution of 4-methyl-3-(2-methylpyrimidin-5-yl)-1-phenyl-1H-pyrazol-5-amine (Preparation B; 2.56 g, 9.64 mmol) in DCM (96 mL) cooled to 0° C. was added triphosgene (1.72 g, 5.78 mmol) in one portion, followed by dropwise addition of DIEA (8.40 mL, 48.20 mmol). The mixture was stirred at 0° C. for 1 hour. (3S,4R)-4-(3-fluorophenyl)-1-(2-methoxyethyl)pyrrolidin-3-amine dihydrochloride (Preparation A; 3.0 g, 9.64 mmol) was added to the mixture in small portions over 10 minutes. The reaction mixture was stirred at ambient temperature for 40 minutes and then poured into water (100 mL). After phase-separation the aqueous layer was extracted with DCM (2×100 mL). The combined organic phases were washed with brine (100 mL), filtered and concentrated. The residue was purified by reverse-phase chromatography (SNAP 120 g C18, 5 to 75% MeOH/water with 0.1% HCl) and dried under vacuum to afford title compound (3.33 g, 57% yield) as a cream-colored foam. MS (apci) m/z=530.3 (M+H).

Example 2

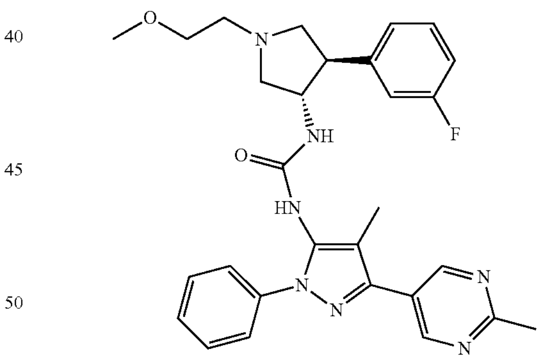

1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea To a suspension of 4-methyl-3-(2-methylpyrimidin-5-yl)-1-phenyl-1H-pyrazol-5-amine (Preparation B; 800 mg, 3.02 mmol) in DCM (15 mL) was added triethylamine (2.1 mL, 15.1 mmol) followed by CDI (587 mg, 3.62 mmol). The mixture was sealed under $N_2$ and stirred at ambient temperature for 22 hours, then treated with (3S,4R)-4-(3-fluorophenyl)-1-(2-methoxyethyl)pyrrolidin-3-amine (Preparation D; 826 mg, 3.47 mmol) in DCM (4 mL). Stirring was continued for 100 minutes. The mixture was partitioned between DCM (60 mL) and water (100 mL). After phase separation, the DCM layer was extracted with 0.5 N HCl (50 mL) and then 0.2 N HCl (2×25 mL). The acid extracts were combined, decanted to a clean flask, placed in a room-temperature water bath and basified with 6N NaOH (aq) and then with 1 N NaOH (aq) to pH 9-10 while stirring. The suspension was stirred in an ice bath for 5 minutes. The resulting solids were filtered, rinsed with water and ether (3×20 mL each) and dried under vacuum to afford the title compound (1.44 g, 90% yield) as a white solid. MS (apci) m/z=530.3 (M+H).

Example 3

Preparation of (3S,4R)-4-(3,4-difluorophenyl)-1-(2-methoxyethyl)pyrrolidin-3-amine (2S,3S)-2,3-bis((4-methylbenzoyl)oxy)succinate Step A: Preparation of (2-Methoxy-N-((trimethylsilyl)methyl)ethanamine: A flask was charged with (chloromethyl)trimethylsilane (3300.0 g, 1.0 eq.), acetonitrile (5.28 L) and 2-methoxyethanamine (4041.0 g, 2.0 eq.). The reaction mixture was stirred at 74° C. for 16 hours and then allowed the reaction to cool to 25° C. Pentane (16 L) was added and the reaction mixture was stirred for 1 minute. The layers were separated. The bottom layer (acetonitrile layer) was added back to the separatory funnel and pentane (16 L) was added to the separatory funnel. After agitation, the layers were separated. The extraction with pentane (16 L) was repeated. The combined pentane layers were added to the separatory funnel and water (3.3 L) was added. After agitation, the layers were separated. MeOH (3.0 L) was added to a 22 L reactor fitted with steam, mechanical stirring, condenser, J-Kem temperature probe, and addition funnel. Atmospheric distillation of solvent was performed at 25°-45° C. During the distillation, the pentane solution was added to the distillation flask by addition funnel at a rate that kept the volume at about 6.6 L until all of the pentane solution was in the distillation flask. Distillation was continued until the total volume in flask was about 6.6 L. The reaction mixture was cooled to 25° C. and stirred at ambient temperature under a nitrogen atmosphere to provide (2-Methoxy-N-((trimethylsilyl)methyl)ethanamine (72% yield).

Step B: Preparation of 2-methoxy-N-(methoxymethyl)-N-((trimethylsilyl)methyl)ethanamine: A flask was charged with (2-methoxy-N-((trimethylsilyl)methyl)ethanamine (380.0 g, 1.0 eq.), methanol (332 mL), and pentane (193 mL) The reaction mixture was stirred in an ice water bath below 5° C. 37% Aqueous formaldehyde (97.9 mL, 1.2 eq.) was added to the reaction mixture at a rate that kept the internal temperature below 10° C., and the reaction mixture was stirred at a temperature below 10° C. for 2 hours. Tert-butyl methyl ether (700 mL, 5.2 eq.) and water (300.0 mL) were added to the reaction mixture, and the mixture was stirred at ambient temperature for about 1 minute. The layers were separated, and organic layer was added back to the separatory funnel. Brine (300 mL) was added to the separatory funnel. The mixture was agitated and the layers were separated. Potassium carbonate $K_2CO_3$ (10.0 g) was added to the organic layer, and after mixing the organic layer was filtered over filter paper. The cake was rinsed with tert-butyl methyl ether. The combined organic layers were concentrated to provide 2-methoxy-N-(methoxymethyl)-N-((trimethylsilyl)methyl)ethanamine as an oil (75% yield).

Step C: Preparation of trans-4-(3,4-difluorophenyl)-1-(2-methoxyethyl)pyrrolidine-3-carboxylic acid: A flask was charged with (E)-3-(3,4-difluorophenyl)acrylic acid (57.0 g, 1.0 eq.), ethyl acetate (143 mL and heptane (143 mL) and the mixture was stirred. Trifluroacetic acid (2.4 mL, 0.1 eq.) was added and the reaction mixture was cooled to below 20° C. 2-Methoxy-N-(methoxymethyl)-N-((trimethylsilyl)methyl) ethanamine was added by addition funnel at a rate that kept the internal temperature between 20° C.-25° C., and the reaction mixture was stirred at 20° C. for 2 hours. The reaction mixture was concentrated under reduced pressure at a temperature between 10° C. and 27° C. Ethyl acetate (200 mL) was added to the residue, and the mixture was concentrated under reduced pressure. The residue was agitated overnight at 20° C. Azetropic removal of impurities was performed by vacuum distillation by adding heptane in portions (total volume: 1200 mL). The resulting slurry was allowed to sit overnight at 20° C. and then filtered over filter paper. The cake was rinsed with heptane and dried in a vacuum oven at 45° C. for about 4 hours to provide trans-4-(3,4-difluorophenyl)-1-(2-methoxyethyl)pyrrolidine-3-carboxylic acid (90% yield).

Step D: Preparation of trans-4-(3,4-difluorophenyl)-1-(2-methoxyethyl)pyrrolidine-3-carboxamide: A flask was charged with trans-4-(3,4-difluorophenyl)-1-(2-methoxyethyl)pyrrolidine-3-carboxylic acid (98.3 g, 1.0 eq.), carbonyl diimidazole (69.8 g, 1.3 eq.), HCl imidazole (7.2 g, 0.2 eq.), and tetrahydrofuran (1000 mL). The reaction mixture was stirred for 1 hour at 25° C. and then overnight at ambient temperature (about 20° C.) under nitrogen. Ammonia (2.0 M in isopropyl alcohol) (307 mL, 1.8 eq.) was added to the reaction mixture over 15 minutes. The reaction mixture was stirred at 25° C. for about 30 minutes. The reaction mixture was filtered over filter paper and the filtered solids were rinsed with EtOAc (200 mL). The combined organic layers were concentrated under reduced pressure at 37° C. Ethyl acetate (200 mL) was added to the resulting crude oil and the mixture was concentrated under reduced pressure at 37° C. Ethyl acetate (200 mL), water (500 mL) and NaCl (82.0 g, 4.1 eq.) were added to the residue and the mixture was stirred for about 2 minutes at ambient temperature. The layers were separated, and the combined organic layers were concentrated under reduced pressure at 37° C. to provide trans-4-(3,4-difluorophenyl)-1-(2-methoxyethyl)pyrrolidine-3-carboxamide (99% yield).

Step E: Preparation of trans-4-(3,4-difluorophenyl)-1-(2-methoxyethyl)pyrrolidin-3-amine: A flask was charged with trans-4-(3,4-difluorophenyl)-1-(2-methoxyethyl)pyrrolidine-3-carboxamide (96.8 g, 1.0 eq.) and methanol (1450 mL) and the reaction mixture was cooled to 5° C. A 10% solution of sodium hypochlorite (462.2 mL, 2.2 eq.) was added by addition funnel at a rate that kept the internal temperature below 20° C. The reaction mixture was stirred for 1 hour at 20° C. and then at 55° C. for 1 hour. Potassium hydroxide (314.6 g, 14.0 eq.) as a solution in water (100 mL) was added to the reaction mixture over 5 minutes, and the reaction mixture was stirred at 72° C.-75° C. for 12 hours. The reaction mixture was cooled to 55° C., and 37 wt % HCl (583.8 mL, 55.9 eq.) was added over 10 minutes to adjust the pH to below 2. Tribasic $K_3PO_4$ (30 wt %, 100.0 mL) was added to adjust the pH of the reaction mixture to be between 6 and 7. The reaction mixture was concentrated under reduced pressure at 37° C. The resulting aqueous mixture was transferred to a separatory funnel, and 30 wt % tribasic $K_3PO_4$ (540.0 mL) and 37 wt % tribasic $K_3PO_4$ (50.0 mL) were added to adjust the pH to ≥10. EtOAc (1000 mL) was added and the mixture was stirred for about 2 minutes at ambient temperature. The layers were separated, and the aqueous layer was added back to the separatory funnel.

EtOAc (500 mL) was added to the separatory funnel, and the mixture was agitated. The layers were separated, and the combined organic layers were concentrated under reduced pressure to provide trans-4-(3,4-difluorophenyl)-1-(2-methoxyethyl)pyrrolidin-3-amine (99% yield).

Step F: Preparation of (3S,4R)-4-(3,4-difluorophenyl)-1-(2-methoxyethyl)pyrrolidin-3-amine (2S,3S)-2,3-bis((4-methylbenzoyl)oxy)succinate: A flask was charged with trans-4-(3,4-difluorophenyl)-1-(2-methoxyethyl)pyrrolidin-3-amine (123.3 g, 1.0 eq.) and methanol (1603 mL). The mixture was stirred at ambient temperature. (2S,3S)-2,3-Bis((4-methylbenzoyl)oxy)succinic acid (145.0 g, 1.5 eq.) and water (295 mL) were added, and the reaction mixture was heated to 65° C. The reaction mixture was seeded with (3S,4R)-4-(3,4-difluorophenyl)-1-(2-methoxyethyl)pyrrolidin-3-amine (2S,3S)-2,3-bis((4-methylbenzoyl)oxy)succinate (0.5 g, 0.7 eq.) (seeds were prepared by performing the reaction on a small scale, which provided the product as a solid), and the reaction mixture was slowly cooled to 25° C. over 16 hours. The slurry was filtered over filter paper. The cake was rinsed with tert-butyl methyl ether (700 mL), and then dried in a vacuum oven at 45° C. for about 4 hours to provide (3S,4R)-4-(3,4-difluorophenyl)-1-(2-methoxyethyl)pyrrolidin-3-amine (2S,3S)-2,3-bis((4-methylbenzoyl)oxy)succinate (35% yield over 2 steps).

Biological Assays

In the biological assays, Compound 1 refers to 1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea; compound 2 refers to 1-((3S,4R)-4-(3,4-difluorophenyl)-1-(2-methoxyethyl)pyrrolidin-3-yl)-3-(4-methyl-3-(2-methylpyrimidin-5-yl)-1-phenyl-1H-pyrazol-5-yl)urea (disclosed in WO 2012/158413); and compound 3 refers to 1-(1',4-dimethyl-1-phenyl-1H,1'H-[3,4'-bipyrazol]-5-yl)-3-((3S,4R)-4-(4-fluorophenyl)-1-(2-methoxyethyl)pyrrolidin-3-yl)urea (disclosed in WO 2012/158413).

Example A

TrkA Kinase Binding Assay

TrkA binding activity was determined in a TrkA LanthaScreen™ Eu Kinase Binding Assay. 5 nM His-tagged recombinant human TrkA (6HIS tagged cytoplasmic domain from Invitrogen, Catalog No. PV3144) was incubated with 4 nM Alexa-Fluor® Tracer 236 (Invitrogen Catalog No. PV5592), 2 nM biotinylated anti-His (Invitrogen Cat. No. PV6090), and 2 nM europium-labeled Streptavidin (Invitrogen Cat. No. PV5899), in buffer (25 mM MOPS, pH 7.5, 5 mM $MgCl_2$, 0.005% Triton X-100). Three fold serial dilutions of Compound 1, compound 2 or compound 3 in DMSO were added to a final percentage of 2% DMSO. After 60-minute incubation at 22° C., the reaction was measured using the EnVision mutlimode plate reader (PerkinElmer) via TR-FRET dual wavelength detection at 615 nM and 665 nM. The percent of control was calculated using a ratiometric emission factor. The $IC_{50}$ value was determined by fitting a four parameter model to the percent of control data.

Compound 1 had an averaged $IC_{50}$ value of 1.1 nM when tested in the assay of Example A. Compound 2 had an averaged $IC_{50}$ value of 1.5 nM when tested in the assay of Example A. Compound 3 had an averaged $IC_{50}$ value of 1.7 nM when tested in the assay of Example A.

Example B

TrkA Cell Assay

CHO-K1 cells transfected with human wild type TrkA were plated in a 96-well flat-bottom plate at $3\times10^5$ cells/well in complete DMEM medium containing 10% FBS and allowed to attach for 24 hours at 37° C., 5% $CO_2$. Medium was then replaced with complete serum free assay medium and the cells were serum starved for 1 hour at 37° C., 5% $CO_2$. Cells were treated with Compound 1, 2 or 3 using 1:3 serial dilutions with final concentrations ranging from 1 μM to 152 μM. The compound was incubated on cells for 1 hour at 37° C., 5% $CO_2$. Cells were then stimulated with a final concentration of 30 ng/mL human NGF for 7 minutes at 37° C., 5% $CO_2$. Medium was removed and cells were lysed with lysis buffer containing phosphatase and protease inhibitors. Phospho-TrkA was measured by ELISA (R&D Catalog No. DYC2578). The ELISA captured total TrkA and detected total phosphor-tyrosine. Optical density was measured for each well using a Versamax reader at a wave length of 450 nm. The $IC_{50}$ values were determined by fitting a four parameter model to the percent of control data.

Compound 1 had an averaged $IC_{50}$ value of 1.9 nM when tested in the assay of Example B. Compound 2 had an averaged $IC_{50}$ value of 1.3 nM when tested in the assay of Example B. Compound 3 had an averaged $IC_{50}$ value of 6.1 nM when tested in the assay of Example B.

Example C

Human Microsomal and Human Hepatocyte Clearance of Compounds 1, 2 and 3

Liver Microsomal Incubations

A 100 mM potassium phosphate assay buffer solution (KPB) was prepared as follows. Both $KH_2PO_4$ and $K_2HPO_4$ were dissolved separately in reagent grade water resulting in final concentrations 100 mM. A 75:25 mixture v/v of $K_2HPO_4$:$KH_2PO_4$ was prepared and the pH of the solution was adjusted to 7.4 using diluted HCl or diluted NaOH solutions. Stock solutions of Compound 1, Compound 2 and Compound 3 were prepared at 10 mM (active compound) in DMSO. The stock solution was diluted immediately before use to 2.5 μM using the KPB solution to create the working standard. All test compounds were completely soluble in DMSO by visual inspection at room temperature. The NADPH-regenerating solution (NRS) was prepared on the day of analysis by diluting one volume of 17 mg/mL $NADP^+$ with one volume of 78 mg/mL glucose-6-phosphate (both prepared in KPB, pH 7.4) and 7.9 volumes of 20 mM $MgCl_2$. The final concentrations of $NADP^+$ and glucose-6-phosphate were 1.7 mg/mL and 7.8 mg/mL, respectively. Immediately prior to use, the NRS was activated by the addition of 10 μL of glucose-6-phosphate dehydrogenase (150 Units/mL in KPB, pH 7.4) per mL of NRS stock solution. Liver microsomes were diluted to 2.5 mg protein/mL using KPB.

For Compound 1, Compound 2, and Compound 3, and each positive control (i.e., dextromethorphan, diazepam, diltiazem, phenacetin, tolbutamide, and verapamil), 20 μL of 2.5 μM working standard solution of test compound and 20 μL of microsomes (2.5 mg protein/mL) were added to each well of a 96-well polypropylene plate (Costar, VWR, West Chester, Pa.) in duplicate. The plates were placed in an incubator at 37° C. for 5 minutes before adding the start solution. A 10-μL aliquot of the NRS solution was added to each original well to initiate metabolism. The concentration of the test compound at the beginning of the incubation was 1 μM. One incubation plate was prepared for each time point (i.e., 0 and 20 minutes). Incubations were conducted at 37° C. and 100% relative humidity. At each time point, the appropriate incubation plate was removed from the incubator and a solution containing internal standard (150 μL, 0.25 μM labetalol in 60% acetonitrile) was added to each well. The plate was immediately spun in a centrifuge at 2,095×g for 7 minutes at room temperature using an Allegra benchtop centrifuge (Beckman Coulter, Fullerton, Calif.). A 200-μL aliquot of the supernatant was transferred from each well to a 96-well shallow plate (Costar). The plates were sealed using reusable plate mats.

Hepatocyte Incubations

Stock solutions of Compound 1, Compound 2, and Compound 3 were prepared at 10 mM (active compound) in DMSO. The in vitro stabilities of Compound 1, Compound 2, and Compound 3 (1 μM) were assessed in the presence of hepatocytes as follows. Cryopreserved hepatocytes were thawed, isolated from shipping media and diluted to a density of $1\times10^6$ viable cells/mL, according to the supplier's guidelines, using Dulbecco's Modified Eagle Medium, 1×, high glucose (DMEM, Invitrogen, Carlsbad, Calif.). Viability was determined by trypan blue exclusion using a hemocytometer (3500 Hausser, VWR, West Chester, Pa.). The 10 mM stock solutions of Compound 1, Compound 2, and Compound 3 were diluted to 2 μM using supplemented DMEM to create the working standard. A 20-μL aliquot of test compound or control (i.e., antipyrine, diazepam, diltiazem, lorazepam, propranolol, verapamil, and 7-ethyl-10-hydroxycamptothecin [SN-38]) was added to each test well of a 96-well polypropylene plate (Costar, VWR, West Chester, Pa.) immediately followed by the addition of 20 μL of the hepatocyte suspension. One incubation plate was prepared for each time point (i.e., 0, 60 and 120 minutes) with samples being prepared in duplicate. Incubations were conducted at 37° C. and 100% relative humidity. At each time point, the appropriate incubation plate was removed from the incubator and a solution containing IS (200 μL, 0.25 μM labetalol in 60% acetonitrile) was added to each well. The plate was mixed at 700 rpm for 1 minute on a plate shaker (IKA MTS 2/4 Digital Microtiter Shaker, VWR) and immediately spun in a centrifuge at 2,095×g for 10 minutes at room temperature using an Allegra benchtop centrifuge (Beckman Coulter, Fullerton, Calif.). A 200-μL aliquot of the supernatant was transferred from each well to a 96-well shallow plate (Costar). The plates were sealed using reusable plate mats.

Calculations

All calculations were performed using BioAssay Enterprise. The mean peak area ratios were calculated by averaging the peak area ratios (n=2) of Compound 1, Compound 2, Compound 3, and the internal standard for each sample. Percent remaining was calculated by determining the ratio of the peak area ratio at each time point to the peak area ratio of the time-zero samples. The rate of loss of test compound ($k_m$) was determined by linear regression of $-\ln(f(t))$ versus time. The regression used the form "y=mx", therefore the model forced an intercept of 100% remaining and assumed that the metabolism followed first order kinetics. The $t_{1/2}$ was determined dividing ln(2) by $k_m$. The predicted intrinsic clearance ($CL_{int}$) was calculated by scaling the in vitro half-life for stability of each of Compound 1, Compound 2, and Compound 3 using physical and physiological scaling factors listed in Table 5 and employed in the following equation:

$$CL_{int} = \frac{\ln 2}{t_{1/2}}\left(\frac{D\cdot W}{C}\right) \quad \text{Eq. 1}$$

where D is the number of hepatocytes per mass of liver for a particular species. W is the average mass of liver present per weight of animal, and C is the number of hepatocytes present during the incubations per unit volume. The predicted hepatic clearance ($CL_h$) was calculated using physical and physiological scaling factors listed in Table 5 and employed in the following equation:

$$CL_h = \frac{CL_{int}\cdot Q}{CL_{int}+Q}$$

where Q is the species-dependent hepatic blood flow. No adjustment was made for the unbound fraction of the test compound ($f_u$). The predicted hepatic extraction ratio (ER) was determined by calculating the ratio of the predicted $CL_h$ to the hepatic blood flow.

$$ER = \frac{CL_h}{Q}$$

TABLE 5

| Species | W[a] | Q[b] | D (mic.)[c] | D (hep.)[d] |
|---|---|---|---|---|
| Mouse | 87.0 | 90 | 50 | 1.20E+08 |
| Rat | 45.0 | 70 | 45 | 1.35E+08 |
| Rabbit | 30.8 | 71 | 78 | 1.20E+08 |
| Dog | 32.0 | 35 | 55 | 1.20E+08 |
| Monkey | 32.0 | 44 | 60 | 1.20E+08 |
| Human | 25.7 | 20 | 53 | 1.20E+08 |

[a]W = average mass of liver (g) per mass of animal (kg).
[b]Q = average hepatic blood flow (mL/min/kg).
[c]D (mic.) = amount of cytochrome P450-related protein (mg) per mass of liver (g).
[d]D (hep.) = number of hepatocytes per mass of liver (g).

Example D

Male Sprague Dawley Rat Pharmacokinetics

Each of Compound 1, Compound 2, and Compound 3 was formulated by adding the compound (dry) to 20% Trappsol® (hydroxypropyl Beta cyclodextrin; CDT, Inc.) (aq) pH 5.0 and vortexing until a homogeneous suspension (PO) or solution (IV) was achieved.

For intravenous dosing, animals were anesthetized with 3% isoflurane, balanced $O_2$. 1 mg/kg of Compound 1, Compound 2, and Compound 3 was administered at a dose volume of 1 mL/kg to the lateral tail vein. Blood was drawn from the opposite lateral tail vein while the animal was under anesthesia (3% isoflurane balanced with $O_2$, 0.2 mL/timepoint) into NaEDTA tubes (1.5% v/v) at the following time points: 1, 5, 15, 30 minutes, and 1, 2, 4, 8 and 24 hours, and mixed thoroughly.

For oral dosing, rats received a single oral dose following an overnight fast. Blood was drawn from the lateral tail vein while the animal was anesthetized with 3% isoflurane balanced with $O_2$ (0.2 mL/timepoint) into NaEDTA tubes (1.5% v/v) at the following time points: 5, 15, and 30 minutes, and 1, 2, 4, 8, 24 and 26 hours, and mixed thoroughly. Following the 24 hour blood collection, animals were redosed orally, and plasma and brain were collected 2 hours post dose for compound analysis. Brains were perefused with saline before removal, weighed and flash frozen in liquid nitrogen until analysis by LCMS/MS. Plasma was separated by centrifugation at 14,000 rpm for 10 minutes and the plasma samples were transferred to 96 well plate tubes with rubber caps and stored at −20±5° C. until analyzed.

Plasma Analysis

A single 12-point calibration curve was prepared by first serially diluting (3-fold) a 40-μg/mL stock solution of Compound 1, Compound 2, and Compound 3 in DMSO to provide standard solutions. Plasma (20 μL) was then added to the extraction plate, and 2.5 μL of each standard solution was added to the naïve plasma. A stock solution of an internal standard (10.0 μL of 2.5 μg/mL in acetonitrile) subsequently was added to each standard and sample solution. Proteinaceous material was precipitated from 20 μL of plasma with the addition of 317.5 μL of acetonitrile for a total volume of 350 μL. Samples were vortex-mixed for 5 minutes and spun in an Allegra X-12R centrifuge (Beckman Coulter, Fullerton, Calif.) for 15 minutes at approximately 1,500×g at 4° C. A 100-μL aliquot of each supernatant was transferred via a 550 μL Personal Pipettor (Apricot Designs, Monrovia, Calif.) to 96-well plates and diluted 1:1 with HPLC grade water. The resulting plates were sealed with plate mats and the amount of Compound 1n the plasma was analyzed by LC-MS/MS.

The LC-MS/MS system was comprised of an HTC-PAL autosampler (Leap Technologies, Inc., Carrboro, N.C.), an HP1100 HPLC (Agilent Technologies Inc., Santa Clara, Calif.), and an API4000 triple quadrupole mass spectrometer (Applied Biosystems, Foster City, Calif.). Chromatographic retention of the analyte and internal standard was achieved using a Phenomenex® Synergi 4μ Hydro-RP 80A column (2.1×30 mm, 4 μm particle size; Phenomenex, Torrance, Calif.) in conjunction with gradient conditions using mobile phases A (10 mM ammonium acetate in aqueous 0.1% formic acid and 1% isopropyl alcohol) and B (10 mM ammonium acetate in 89.9% acetonitrile, 10% methanol, 0.1% formic acid). The total run time, including re-equilibration time, for a single injection was 3.5 minutes and the flow rate was 0.8 mL/minute. Solvent B was increased from 5 to 95% in 1.0 minute, held at 95% for 1.0 minute, and then decreased to 5% in 0.1 minute.

| Time (min) | Mobile Phase A (%) | Mobile Phase B (%) |
|---|---|---|
| 0.00 | 95 | 5 |
| 0.25 | 95 | 5 |
| 1.25 | 5 | 95 |
| 2.25 | 5 | 95 |
| 2.35 | 95 | 5 |
| 3.50 | 95 | 5 |

Brain Analysis

A single 12-point calibration curve was prepared by first serially diluting (3-fold) a 40-μg/mL stock solution of each of Compound 1, Compound 2, and Compound 3 in DMSO. Brain homogenate was prepared by adding 5.0 mL of water to conical 50 mL tubes containing brains. The contents of the tubes were homogenized using an Omni-Prep Multi Sample Homogenizer (Kennesaw, Ga.) at 22,000 RPM for 180 seconds. The homogenate (100 μL) was added to the extraction plate, and 2.5 μL each standard solution was added to the naïve brain homogenate. A stock solution of an internal standard (10.0 μL of 2.5 μg/mL in acetonitrile) subsequently was added to each standard and sample solution. Proteinaceous material was precipitated from 100 μL of mouse tumor homogenate with the addition of 237.5 μL of acetonitrile for a total volume of 350 μL. Samples were vortex-mixed for 5 minutes and spun in an Allegra X-12R centrifuge (Beckman Coulter, Fullerton, Calif.) for 15 minutes at approximately 1,500×g at 4° C. A 100-μL aliquot of each supernatant was transferred via a 550 μL Personal Pipettor (Apricot Designs, Monrovia, Calif.) to 96-well plates and diluted 1:1 with HPLC grade water. The resulting plates were sealed with plate mats and the amount of Compound 1n the brain was analyzed by LC-MS/MS.

The LC-MS/MS system was comprised of an HTC-PAL autosampler (Leap Technologies, Inc., Carrboro, N.C.), an HP1100 HPLC (Agilent Technologies Inc., Santa Clara, Calif.), and an API4000 triple quadrupole mass spectrometer (Applied Biosystems, Foster City, Calif.). Chromatographic retention of the analyte and internal standard was achieved using a Phenomenex® Synergi 4μ Hydro-RP 80A column (2.1×30 mm, 4 μm particle size; Phenomenex, Torrance, Calif.) in conjunction with gradient conditions using mobile phases A (10 mM ammonium acetate in aqueous 0.1% formic acid and 1% isopropyl alcohol) and B (10 mM ammonium acetate in 89.9% acetonitrile, 10% methanol, 0.1% formic acid).

| Time (min) | Mobile Phase A (%) | Mobile Phase B (%) |
|---|---|---|
| 0.00 | 95 | 5 |
| 0.25 | 95 | 5 |
| 1.25 | 5 | 95 |
| 2.25 | 5 | 95 |
| 2.35 | 95 | 5 |
| 3.50 | 95 | 5 |

The total run time, including re-equilibration time, for a single injection was 3.5 minutes and the flow rate was 0.8 mL/min. Solvent B was increased from 5 to 95% in 1.0 minutes, held at 95% for 1.0 minute, and then decreased to 5% in 0.1 minute. Mass spectrometric detection of the analytes was accomplished using ESI+ ionization mode. Ion current was optimized during infusion of a stock solution of Compound 1, Compound 2, and Compound 3. Analyte responses were measured by multiple reaction monitoring (MRM) of transitions unique to each compound. Pharmacokinetic parameters were calculated by established non-compartmental modeling using an in-house proprietary software (Sherlock Version 2.1). AUC's were calculated using linear trapezoidal integration.

Example E

Dog Pharmacokinetics

An IV dose formulation for delivery of a 1 mg/kg in 1 mL/kg dose volume was prepared as follow. The vehicle for the formulation was 20% Trappsol® (hydroxypropyl Beta cyclodextrin; CDT, Inc.) (aq) in water. A final volume of the vehicle was added to each of Compound 1, Compound 2, and Compound 3 (as dry compounds) and the mixture was stirred until a homogeneous solution was obtained. The pH of the final solution was 7. The solution was filtered using a 0.2 μM filter before delivering to the animal.

Male Beagle dogs received a single intravenous dose following an overnight fast. Blood/plasma was collected (1.5 mL/timepoint) in $K_2$EDTA blood collection tubes at the following time points post-dose: 0, 1, 5, 15, and 30 minutes, and 1, 2, 4, 8, 12, 24, and 48 hours, and mixed thoroughly. Blood samples were collected from the jugular, cephalic or saphenous veins from conscious animals. Blood samples were kept on ice until processed for plasma. Blood samples were centrifuged at 3200 RPM for 10 minutes at approximately 5° C. Plasma samples were directly transferred to 96-well plate tubes (MatrixTech, 0.75 mL). Rubber injectable caps were placed on the 96-well plate tubes. Plasma samples were stored at −20±5° C. until analyzed.

Plasma Analysis

A single 12-point calibration curve was prepared by first serially diluting (3-fold) a 40-μg/mL stock solution of Compound 1, Compound 2, and Compound 3 in DMSO to provide standard solutions. Plasma (20 μL) was then added to the extraction plate, and 2.5 μL of each standard solution was added to the naïve plasma. A stock solution of an internal standard (10.0 μL of 2.5 μg/mL in acetonitrile) subsequently was added to each standard and sample solution. Proteinaceous material was precipitated from 20 μL of plasma with the addition of 317.5 μL of acetonitrile for a total volume of 350 μL. Samples were vortex-mixed for 5 minutes and spun in an Allegra X-12R centrifuge (Beckman Coulter, Fullerton, Calif.) for 15 minutes at approximately 1,500×g at 4° C. A 100-μL aliquot of each supernatant was transferred via a 550 μL Personal Pipettor (Apricot Designs, Monrovia, Calif.) to 96-well plates and diluted 1:1 with HPLC grade water. The resulting plates were sealed with plate mats and the amount of Compound 1 n plasma was analyzed by LC-MS/MS.

The LC-MS/MS system was comprised of an HTC-PAL autosampler (Leap Technologies, Inc., Carrboro, N.C.), an HP1100 HPLC (Agilent Technologies Inc., Santa Clara, Calif.), and an API4000 triple quadrupole mass spectrometer (Applied Biosystems, Foster City, Calif.). Chromatographic retention of the analyte and internal standard was achieved using a Phenomenex® Synergi 4μ Hydro-RP 80A column (2.1×30 mm, 4 μm particle size; Phenomenex, Torrance, Calif.) in conjunction with gradient conditions using mobile phases A (10 mM ammonium acetate in aqueous 0.1% formic acid and 1% isopropyl alcohol) and B (10 mM ammonium acetate in 89.9% acetonitrile, 10% methanol, 0.1% formic acid). The total run time, including re-equilibration time, for a single injection was 3.5 minutes and the flow rate was 0.8 mL/minute. Solvent B was increased from 5 to 95% in 1.0 minute, held at 95% for 1.0 minute, and then decreased to 5% in 0.1 minute.

| Time (min) | Mobile Phase A (%) | Mobile Phase B (%) |
|---|---|---|
| 0.00 | 95 | 5 |
| 0.25 | 95 | 5 |
| 1.25 | 5 | 95 |
| 2.25 | 5 | 95 |
| 2.35 | 95 | 5 |
| 3.50 | 95 | 5 |

Mass spectrometric detection of the analytes was accomplished using ESI+ ionization mode. Ion current was optimized during infusion of a stock solution of Compound 1, Compound 2, and Compound 3. Analyte responses were measured by multiple reaction monitoring (MRM) of transitions unique to each compound. Pharmacokinetic parameters were calculated by established non-compartmental modeling using an in-house proprietary software (Sherlock Version 2.1). AUC's were calculated using linear trapezoidal integration.

Example F

FASTPatch® hERG Assay

This assay was used to measure the effects of Compound 1, Compound 2, and Compound 3 on cloned hERG potassium channels expressed in human embryonic kidney cells (HEK293). The in vitro effects of Compound 1, Compound 2, and Compound 3 on the hERG (human ether-a-go-go-related gene) potassium channel current (a surrogate for IKr, the rapidly activating, delayed rectifier cardiac potassium current) expressed in mammalian cells were evaluated at room temperature using the QPatch HT® (Sophion Bioscience A/S, Denmark), an automatic parallel patch clamp system. The test article was evaluated at 0.3, 1, 3, 10, 30 and 100 μM with each concentration tested in three or more cells (n≥3). The duration of exposure to each test article concentration was 3 minutes. A positive control confirmed the sensitivity of the test system to hERG inhibition.

Example G

D38 Kinase Binding Assay

The p38α binding activity of Compound 1 was determined in a p38α LanthaScreen™ Eu Kinase Binding Assay. 5 nM of inactive, GST-tagged recombinant human p38α (GST-tagged cytoplasmic domain from Invitrogen, Catalog No. PV3305) was incubated with 5 nM Alexa-Fluor® Tracer 199 (Invitrogen Cat. No. PV5830), and 2 nM europium labeled anti-GST antibody (Invitrogen Cat. No. PV5594), in buffer (25 mM [$Na^+$] HEPES pH 7.3, 10 mM $MgCl_2$, 100 μM $NaVO_4$). Three fold serial dilutions of Compound 1 in DMSO were added to a final percentage of 2% DMSO. After 60-minute incubation at 22° C., the reaction was measured using the EnVision multimode plate reader (PerkinElmer) via TR-FRET dual wavelength detection at 615 nM and 665 nM. The percent of control was calculated using a ratiometric emission factor. The $IC_{50}$ value was determined by fitting a four parameter model to the percent of control data. Compound 1 was found to be 1000 fold more potent against TrkA than p38α.

Example H

Off-Target Kinase Profiling

Compound 1 was tested for off-target kinase activity at a concentration of 10 μM by Millipore, Inc. in their KinaseProfiler™ service against all the kinases available in their full kinase panel. Compound 1 was run in duplicate at a concentration of ATP near the Km for each individual kinase according to Millipore's specifications. The results are shown in the Table below. Data are reported as percent of control (POC) and are the average of the two replicates.

In the KinaseProfiler™ Compound 1 showed remarkable and unexpected selectivity for inhibiting TrkA versus other kinases in the panel. In fact, Compound 1 was largely inactive against off-target kinases at a concentration of 10 μM, and thus would not be expected to inhibit off-target kinases at therapeutic doses in mammals. The ability of Compound 1 to selectively inhibit the Trk pathway without inhibiting other off-target kinases could translate into a drug profile that is essentially free of side-effects related to inhibition of off-target kinases. Such a drug profile would represent a safer approach to treating pain, inflammation, cancer and certain skin diseases than has been previously reported.

| Kinase | Compound 1 Avg POC |
|---|---|
| AKT1 | 104 |
| AKT2 | 104.5 |
| AKT3 | 113.5 |
| DMPK | 98.5 |
| GRK5 | 100 |
| GRK6 | 98 |
| GRK7 | 101 |
| MRCKalpha | 90.5 |
| MRCKbeta | 106.5 |
| MSK1 | 129 |
| MSK2 | 116.5 |
| p70S6K | 104 |
| PDK1 | 104 |
| PKAC-alpha | 129.5 |
| PKCalpha | 98.5 |
| PKCbetaI | 102.5 |
| PKCbetaII | 99.5 |
| PKCdelta | 102 |
| PKCepsilon | 101.5 |
| PKCeta | 100 |
| PKCgamma | 98 |
| PKCiota | 91 |
| PKCtheta | 128.5 |
| PKCzeta | 97.5 |
| PRK2 | 116 |
| PRKG1alpha | 109.5 |
| PRKG1beta | 95.5 |
| PrKX | 115.5 |
| ROCK-I | 98.5 |
| ROCK-II | 105.5 |
| Rsk1 | 102 |
| Rsk2 | 93 |
| Rsk3 | 107.5 |
| Rsk4 | 105.5 |
| SGK1 | 105 |
| SGK2 | 112 |
| SGK3 | 112.5 |
| eEF-2K | 112.5 |
| mTOR | 97.5 |
| mTOR/FKBP12 | 105.5 |
| AMPK(A1/B1/G1) | 102.5 |
| ARK5 | 104.5 |
| BrSK1 | 98 |
| BrSK2 | 104 |
| CAMK1 | 104.5 |
| CAMK1d | 130 |
| CAMK2b | 147.5 |
| CAMK2d | 97.5 |
| CAMK2g | 97 |
| CAMK4 | 100 |
| CHK1 | 109 |
| CHK2 | 102.5 |
| DAPK1 | 114 |
| DAPK2 | 97 |
| DAPK3 | 105.5 |
| DCAMKL2 | 135 |
| DRAK1 | 129.5 |
| LKB1 | 104.5 |
| MAPKAP-K2 | 115 |
| MAPKAP-K3 | 99 |
| MAPKAP-K5 | 89.5 |
| MARK1 | 100 |
| MARK2 | 109.5 |
| MELK | 105.5 |
| MKNK2 | 111 |
| MYLK | 106.5 |
| PASK | 137.5 |
| PhKgamma2 | 108 |
| Pim-1 | 103.5 |
| Pim-2 | 117.5 |
| Pim-3 | 106.5 |
| PKD1 | 94.5 |
| PKD2 | 94.5 |
| SIK | 108 |

-continued

| Kinase | Compound 1 Avg POC |
|---|---|
| STK33 | 101 |
| TSSK1 | 104 |
| TSSK2 | 108.5 |
| CK1_y | 91.5 |
| CK1delta | 104 |
| CK1gamma1 | 78.5 |
| CK1gamma2 | 61.5 |
| CK1gamma3 | 104.5 |
| VRK2 | 96 |
| CDK1/cyclinB | 108 |
| CDK2/cyclinA | 94.5 |
| CDK2/cyclinE | 102 |
| CDK3/cyclinE | 94.5 |
| CDK5/p25 | 115 |
| CDK5/p35 | 97 |
| CDK6/cyclinD3 | 99.5 |
| CDK7/cyclinH/MAT1 | 99 |
| CDK9/cyclinT1 | 112 |
| CLK2 | 102 |
| CLK3 | 94.5 |
| DYRK2 | 102 |
| ERK1 | 94.5 |
| ERK2 | 100 |
| GSK3alpha | 109.5 |
| GSK3beta | 112 |
| HIPK1 | 98.5 |
| HIPK2 | 101.5 |
| HIPK3 | 90 |
| JNK1alpha1 | 95 |
| JNK2alpha2 | 98.5 |
| JNK3 | 114.5 |
| MSSK1 | 127.5 |
| NLK | 94.5 |
| p38alpha | 107.5 |
| p38beta | 102 |
| p38delta | 105 |
| p38gamma | 114.5 |
| SRPK1 | 96 |
| SRPK2 | 96.5 |
| AURKA | 115 |
| CK2alpha2 | 106 |
| Haspin | 96.5 |
| IKKalpha | 101.5 |
| IKKbeta | 104.5 |
| NEK11 | 94 |
| NEK2 | 95 |
| NEK3 | 104.5 |
| NEK6 | 96 |
| NEK7 | 104 |
| Plk1 | 99.5 |
| Plk2 | 101 |
| Plk3 | 100.5 |
| TBK1 | 114.5 |
| TLK2 | 101.5 |
| ULK2 | 106 |
| ULK3 | 107.5 |
| WNK2 | 92.5 |
| WNK3 | 115.5 |
| LOK | 125.5 |
| MAP3K5 | 101 |
| MAP4K2 | 101 |
| MEK1 | 103.5 |
| MINK | 105 |
| MKK4_m | 125 |
| MKK6 | 107.5 |
| MKK7 | 125 |
| MST1 | 107.5 |
| MST2 | 102 |
| MST3 | 103.5 |
| PAK2 | 105.5 |
| PAK4 | 97 |
| PAK5 | 111 |
| PAK6 | 114.5 |
| TAO1 | 96 |
| TAO2 | 100 |
| TAO3 | 103 |
| Abl2 | 110.5 |

-continued

| Kinase | Compound 1 Avg POC |
|---|---|
| Abl-P | 110.5 |
| ALK | 89 |
| Axl | 115.5 |
| BLK | 82.5 |
| Bmx | 91.5 |
| BTK | 114 |
| CSK | 100 |
| DDR2 | 121.5 |
| EGFR | 95.5 |
| EphA1 | 94.5 |
| EphA2 | 92.5 |
| EphA3 | 95.5 |
| EphA4 | 98 |
| EphA5 | 109.5 |
| EphA7 | 109 |
| EphA8 | 110 |
| EphB1 | 105.5 |
| EphB2 | 98 |
| EphB3 | 89.5 |
| EphB4 | 102 |
| ErbB4 | 107.5 |
| FAK | 100.5 |
| FAK2 | 92.5 |
| Fer | 103.5 |
| Fes | 102.5 |
| FGFR1 | 117 |
| FGFR2 | 99 |
| FGFR3 | 108 |
| FGFR4 | 105 |
| Fgr | 106 |
| Flt1 | 97 |
| Flt3 | 102 |
| Flt4 | 98.5 |
| Fms | 103 |
| Fyn | 96.5 |
| Hck | 108.5 |
| IGF-1R | 80.5 |
| IGF-1R Activated | 105 |
| IR | 84.5 |
| IR Activated | 105.5 |
| IRR | 104.5 |
| ITK | 104 |
| JAK2 | 126 |
| JAK3 | 95.5 |
| KDR | 102.5 |
| KIT | 97.5 |
| Lck | 94 |
| Lyn | 104.5 |
| Mer | 147.5 |
| Met | 124.5 |
| MuSK | 95 |
| PDGFRalpha | 96 |
| PDGFRbeta | 96 |
| PTK5 | 105 |
| PTK6 | 106 |
| Ret | 111.5 |
| Ron | 100 |
| Ros | 112.5 |
| Rse | 102.5 |
| Src | 120 |
| Syk | 95.5 |
| TEC Activated | 97 |

-continued

| Kinase | Compound 1 Avg POC |
|---|---|
| Tie2 | 82 |
| TNK2 | 93.5 |
| TrkA | 2.5 |
| TrkB | 1.5 |
| Txk | 67 |
| Yes | 98.5 |
| ZAP-70 | 104.5 |
| ALK4 | 106.5 |
| c-RAF | 101 |
| IRAK1 | 103 |
| IRAK4 | 98 |
| LIMK1 | 98 |
| MLK1 | 109.5 |
| RIPK2 | 90.5 |
| TAK1-TAB1 | 101.5 |

What is claimed is:

1. A Compound

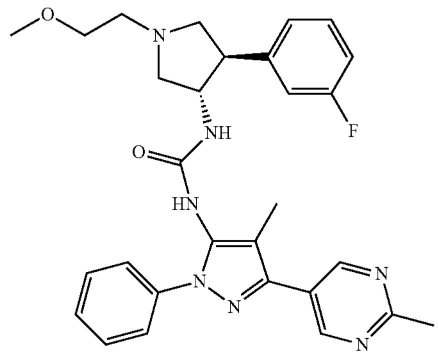

1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea, or a pharmaceutically acceptable salt thereof.

2. The compound according to claim 1, wherein the compound is a dihydrochloride salt of 1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea.

3. A pharmaceutical composition, which comprises a compound of claim 1, and a pharmaceutically acceptable diluent or carrier.

4. The pharmaceutical composition of claim 3, wherein said pharmaceutical composition is formulated for oral administration.

5. The pharmaceutical composition of claim 4, wherein said pharmaceutical composition is in the form of a tablet or capsule.

* * * * *